US011328090B2

(12) United States Patent
van't Noordende

(10) Patent No.: US 11,328,090 B2
(45) Date of Patent: May 10, 2022

(54) METHODS AND SYSTEMS FOR PROVIDING ACCESS TO CONFIDENTIAL INFORMATION

(71) Applicant: Northend Systems B.V., Amsterdam (NL)

(72) Inventor: Guido Johannes van't Noordende, Amsterdam (NL)

(73) Assignee: Northend Systems B.V., Amsterdam (NL)

( * ) Notice: Subject to any disclaimer, the term of this patent is extended or adjusted under 35 U.S.C. 154(b) by 282 days.

(21) Appl. No.: 16/633,913

(22) PCT Filed: Jul. 25, 2018

(86) PCT No.: PCT/NL2018/050519
§ 371 (c)(1),
(2) Date: Jan. 24, 2020

(87) PCT Pub. No.: WO2019/022604
PCT Pub. Date: Jan. 31, 2019

(65) Prior Publication Data
US 2021/0150051 A1    May 20, 2021

(30) Foreign Application Priority Data

Jul. 26, 2017   (NL) .................................... 2019349

(51) Int. Cl.
*G06F 21/62* (2013.01)
*G16H 10/60* (2018.01)
(Continued)

(52) U.S. Cl.
CPC ......... *G06F 21/6245* (2013.01); *G16H 10/60* (2018.01); *H04L 9/06* (2013.01); *H04L 63/18* (2013.01); *G06F 21/6263* (2013.01)

(58) Field of Classification Search
CPC . G06F 21/6245; G06F 21/6263; G16H 10/60; H04L 9/06; H04L 63/18
See application file for complete search history.

(56) References Cited

U.S. PATENT DOCUMENTS

| 8,613,105 | B2 * | 12/2013 | Shaikh ................ G06F 21/6272 726/28 |
| 10,366,204 | B2 * | 7/2019 | Tanner, Jr. ............. G16H 40/20 |

(Continued)

FOREIGN PATENT DOCUMENTS

| DE | 10121819 A1 * | 11/2002 | ............. G16H 10/60 |
| WO | WO-2012078898 A2 * | 6/2012 | ............. G16H 10/65 |
| WO | WO-2014090411 A1 * | 6/2014 | ............. G06F 21/46 |

OTHER PUBLICATIONS

Kierkegaard, "Eletronic heath record: Wiring Europe's healthcare", Computer Law & Security Report, Sep. 30, 2011, pp. 503-515, vol. 27, No. 5.

(Continued)

*Primary Examiner* — Shahriar Zarrineh
(74) *Attorney, Agent, or Firm* — The Webb Law Firm

(57) ABSTRACT

This disclosure relates to systems and methods for providing a client system access to confidential information of a person stored at a source system, the client system being configured to access the confidential information using a resource identifier, the client system and the source system comprising an encryption module for executing an encryption algorithm.

11 Claims, 6 Drawing Sheets

(51) Int. Cl.
*H04L 9/06* (2006.01)
*H04L 29/06* (2006.01)

(56) References Cited

U.S. PATENT DOCUMENTS

| | | | |
|---|---|---|---|
| 2002/0158911 A1* | 10/2002 | O'Rourke | G06F 3/0481 715/810 |
| 2002/0161795 A1* | 10/2002 | O'Rourke | G16H 10/60 715/205 |
| 2004/0034550 A1* | 2/2004 | Menschik | G16H 70/20 705/3 |
| 2004/0107367 A1* | 6/2004 | Kisters | G07F 7/1008 726/9 |
| 2006/0059111 A1* | 3/2006 | Tucker | G06F 21/31 705/75 |
| 2008/0306872 A1* | 12/2008 | Felsher | G06Q 20/367 705/51 |
| 2010/0024042 A1* | 1/2010 | Motahari | G06Q 10/10 726/26 |
| 2010/0191972 A1* | 7/2010 | Kiliccote | G06F 21/606 713/172 |
| 2012/0177256 A1* | 7/2012 | Keefe | G16H 10/60 382/115 |
| 2013/0006865 A1* | 1/2013 | Spates | H04L 63/062 705/50 |
| 2014/0047513 A1* | 2/2014 | van'T Noordende | H04L 63/0823 726/4 |
| 2014/0089008 A1* | 3/2014 | Carner | G06Q 10/00 705/3 |
| 2014/0222684 A1* | 8/2014 | Felsher | G16H 10/60 705/50 |
| 2016/0147945 A1 | 5/2016 | MacCarthy et al. | |

OTHER PUBLICATIONS

Markle Foundation, "Record Locator Service—Technical Background from the Massachusetts Prototype Community", Jan. 1, 2006, pp. 1-77.

* cited by examiner

| # | ID | ID_contracted | AC | EID | RI |
|---|---|---|---|---|---|
| 1 | 999901230 | 901230 | 123456 | 795182 | https://sourcesyst102.org/recordID=9537 |
| 2 | 999901230 | 901230 | 654783 | 277969 | https://sourcesyst102.org/recordID=5674 |
| 3 | 999901230 | 901230 | 923874 | 252044 | https://sourcesyst102.org/recordID=5735 |
| 4 | 164154553 | 154553 | 761928 | 654321 | https://sourcesyst102.org/recordID=6782 |
| 5 | 265413 | - | 874321 | 613268 | https://sourcesyst102.org/recordID=3233 |

| # | RI | EID |
|---|---|---|
| 1 | https://sourcesyst102.org/recordID=9537 | 795182 |
| 2 | https://sourcesyst102.org/recordID=5674 | 277969 |
| 3 | https://sourcesyst102.org/recordID=5735 | 252044 |
| 4 | https://sourcesyst102.org/recordID=6782 | 654321 |
| 5 | https://sourcesyst102.org/recordID=3233 | 613268 |
| 6 | https://sourcesyst999.org/recordID=6489 | 498768 |

METHODS AND SYSTEMS FOR PROVIDING ACCESS TO CONFIDENTIAL INFORMATION

CROSS-REFERENCE TO RELATED APPLICATIONS

This application is the United States national phase of International Application No. PCT/NL2018/050519 filed Jul. 25, 2018, and claims priority to Netherlands Patent Application No. 2019349 filed Jul. 26, 2017, the disclosures of which are hereby incorporated by reference in their entirety.

FIELD OF THE INVENTION

This invention relates to methods for providing a client system access to confidential information stored at a source system. The invention further relates to a system, source system, client system, server system, computer program product and a computer-readable storage medium for performing these methods.

BACKGROUND OF THE INVENTION

Due to the rising complexity of healthcare, doctors increasingly need to exchange medical information about patients between different organizations. Electronic communication of medical information can be highly efficient, yet must respect the privacy of patients and comprise appropriate security measures to minimize the risk of confidential information being disclosed to unauthorized parties.

Different centralized architectures to manage access to medical records are known. One example is the Dutch National Switching Point or LSP, which employs a "switching point" that centrally controls access to medical records of patients. These records are stored in many different (physical) locations in the systems of the healthcare organizations. The central switching point contains, per patient, one or more "pointers", so it can request information from locations at which medical records are stored. In an example, a medical record of person A is stored in the system of a gynaecologist B, and another record containing medical information is stored with a pharmacist C. The switching point D, upon receiving from a doctor E an electronically signed request to obtain the records of person A, checks, using a certificate vouching for doctor E's identity and credentials that is sent along with the signed request, whether said doctor E is allowed access. If this is the case, the switching point D, internally, looks up the storage location of the medical records. Next, the switching point sends a request to systems B and C for the medical records stored there. Then, the medical records are returned to the switching point D, which forwards it to the client system of the doctor E who requested the record.

A disadvantage of architectures that implement centralized access control is that the central system is in a position to facilitate (after compromise) possible illegitimate requests for medical records that are stored in decentral systems that hold patient information (source systems). Since the source systems which are connected to such a system must trust the central authorization component, an attacker who gains access to the central authorization component may effectively obtain any medical record by sending illegitimate requests. Further, since access control is typically governed using a generic role-based access control policy, there may be many access points which, if compromised, may provide an entry point for illegitimate access to a patient record; in other words, the multiple (large number of) access points form a large 'attack surface'.

An example of a decentralized architecture for providing access to confidential information in a way that alleviates some of the problems outlined above, is described in US 2014/0047513 A1. Herein a source system—and the healthcare organization or healthcare professional responsible for the records therein—containing medical records maintain full control over the disclosure of medical records, by actively pushing authorizations to parties who may access medical records, and by enforcing that only the holder of an authorization may obtain the medical records. The source system, in providing access to a medical record, generates a reference to the medical record of a patient, which typically takes the form of a URL. The source system can subsequently bind this reference to a specific health professional or client system, wherein the binding comprises associating the reference to the specific health professional or client system. The health professional or the client system that he or she uses is typically identified (authenticated) using a key; thus, a binding in the typical case is an association between a reference (URL) and a client key.

The binding can take place up-front, or at first use. In the latter case, the process may involve the patient to carry a "token" or a (temporary) PIN, or another out-of-band mechanism for transporting such token or PIN, to the party who is involved with treatment and who is supposed to obtain the patient information, where the receiving party's client system upon using the URL must (first) be able to demonstrate that it has access to the token or PIN before the URL is bound to this client system.

As a consequence of the binding, only the bound client system can use the reference to initiate a request for obtaining the medical record, or to initiate another operation on the reference or on the medical record that the reference points to. The source system namely is configured to verify, upon receiving a request for a medical record from a client system, that that client system is indeed bound to the reference that was used to initiate the request. If the source system determines that a wrong client system has obtained and used a reference, the source system will not accept its request. Wrong client system here may be understood as a client that is not bound to (associated with) the reference.

An advantage of this architecture is that the keeper of a medical record, for example a general practitioner, stays in full control as to whom exactly (to which client [systems] exactly) he provides access for a specific medical record. Each authorized party/system holds his own, unique, bound reference (URL), making all authorizations in the system easily tractable and revocable, if necessary.

In practice, however, there are situations wherein a reference cannot be bound to a particular doctor or client system a priori, that is, immediately upon generation of the reference. In an example, a general practitioner will prescribe medication to a patient. For medical reasons, the general practitioner may be compelled to provide access to some of the medication information he holds about the patient to a pharmacist. However, as the patient may fill the prescription at any pharmacist, as is the case in the Netherlands, the reference to the medical records of the patient cannot be a priori bound to one specific pharmacist up front. Simply placing an unbound reference in a widely accessible (temporary) index or other widely available storage system or server, poses a security risk since unbound references, notwithstanding additional security measures, can be used by any one of potentially a large group/set of client systems to request a medical record of a patient.

Hence, there is a need in the art for improved methods for providing a client system access to confidential information in a secure way, which is also convenient to use in practice, that is, for an improved method that enables to employ unbound references in the context of named decentralized architecture in a secure and usable manner, or possibly in systems that use URLs in general in situations where the eventual user of the URL is not a priori known.

SUMMARY

It is the object of the present disclosure to provide an improved method for disclosing confidential information, wherein the method enables improved protection of confidential information that is stored at a specific location, while allowing access to this data in an efficient yet highly controllable way.

Therefore this disclosure relates to a method for providing a client system access to confidential information of a person stored at a source system, the client system being configured to access the confidential information using a resource identifier, the client system and the source system comprising an encryption module for executing an encryption algorithm. The method comprises the source system generating the resource identifier, preferably the resource identifier comprising a URL or at least part of a URL, the resource identifier being indicative of a data storage location at the source system, the data storage location comprising the confidential information of the person, the person being identified by a person identifier. The method further comprises the source system obtaining, for example generating or receiving, a first code and the source system using the encryption algorithm for generating a second code based on the first code and based on the person identifier. The method also comprises the source system transmitting a message to a server system, the message comprising at least part of the resource identifier, the message instructing the server system to store the first code or the second code as an encrypted person identifier in association with the at least part of the resource identifier. The method further comprises the source system providing the second code or the first code respectively as authorization code to a trusted communication path for delivery of the authorization code to the client system. The method also comprises the source system receiving from a client system a request to access the confidential information associated with the person identifier, wherein the client system is adapted to receive the authorization code via the trusted communication path and to receive the person identifier in order to generate the encrypted person identifier based on the received authorization code and based on the received person identifier using the encryption algorithm; and to retrieve the at least part of the resource identifier from the server system on the basis of the generated encrypted person identifier; and, to use the at least part of the resource identifier for sending the request to the source system. The method further comprises the source system providing the client system access to the confidential information on the basis of the request received from the client system, wherein providing access includes retrieving the confidential information from the data storage location and transmitting at least part of the confidential information to the client system.

Optionally, the method comprises the source system receiving from the client system the authorization code obtained by the client system and the source system providing the client system access to the confidential information on the basis of the received request message and on the basis of the authorization code received from the client system.

Optionally, the method comprises in response to receiving the request message from the client system, the source system instructing the client system to provide the authorization code.

In another aspect the disclosure relates to a source system for providing a client system access to confidential information of a person stored at a source system, the client system being configured to access the confidential information using a resource identifier, the client system and the source system comprising an encryption module for executing an encryption algorithm, the source system comprising a computer readable storage medium having at least part of a program embodied therewith and a computer readable storage medium having computer readable program code embodied therewith, and a processor, preferably a microprocessor, coupled to the computer readable storage medium, wherein responsive to executing the computer readable program code, the processor is configured to perform executable operations comprising one or more of the method steps, e.g. the method steps executed by a source system, as disclosed herein.

In another aspect the disclosure relates to a method for a client system for accessing confidential information of a person stored at a source system, the client system being configured to access the confidential information using a resource identifier, the client system and the source system comprising an encryption module for executing an encryption algorithm, wherein the source system is configured to generate the resource identifier, preferably the resource identifier comprising a URL, the resource identifier being indicative of a data storage location at the source system, the data storage location comprising the confidential information of the person, the person being identified by a person identifier, and to obtain, for example generate or receive, a first code; and to use the encryption algorithm for generating a second code based on the first code and based on the person identifier; and to transmit a message to a server system, the message comprising at least part of the resource identifier, the message instructing the server system to store the first code or the second code as an encrypted person identifier in association with the at least part of the resource identifier; and to provide the second code or the first code respectively as authorization code to a trusted communication path for delivery of the authorization code to the client system; the method comprising the client system receiving the authorization code via the trusted communication path, the client system receiving the person identifier, the client system using the encryption algorithm to generate the encrypted person identifier based on the received authorization code and based on the received person identifier, the client system transmitting a request message to the server system, the request message comprising the encrypted person identifier as generated by the client system, the request message requesting the server system to provide the at least part of the resource identifier, the client system receiving the at least part of the resource identifier from the server system, the client system using the at least part of the resource identifier for sending a request to access the confidential information to the source system; wherein the source system is configured to provide the client system access to the confidential information on the basis of the request received from the client system, the method further comprising the client system gaining access to the confidential information by receiving at least part of the confidential information from the source system.

Optionally this method comprises the client system providing the obtained authorization code to the source system.

Optionally this method comprises the client system receiving from the source system an instruction to provide the authorization code to the source system and in response providing the authorization code to the source system.

In another aspect the disclosure relates to a client system for accessing confidential information stored at a data storage location of a source system, the data storage location comprising the confidential information of a person, the person being identified by a person identifier; the client system being configured to access the confidential information using a resource identifier, the client system comprising a computer readable storage medium having at least part of a program embodied therewith; and, a computer readable storage medium having computer readable program code embodied therewith, and a processor, preferably a microprocessor, coupled to the computer readable storage medium, wherein responsive to executing the computer readable program code, the processor is configured to perform executable operations comprising one or more of the method steps, e.g. the method steps executed by a client system, as disclosed herein.

In another aspect the disclosure relates to a method for enabling a client system to access confidential information of a person stored at a source system, the client system being configured to access the confidential information using a resource identifier, the client system and the source system comprising an encryption module for executing an encryption algorithm, wherein the source system is configured to generate the resource identifier, preferably the resource identifier comprising a URL, the resource identifier being indicative of a data storage location at the source system, the data storage location comprising the confidential information of the person, the person being identified by a person identifier; and to obtain, for example generate or receive, a first code; and to use the encryption algorithm for generating a second code based on the first code and based on the person identifier; and to provide the second code or the first code respectively as authorization code to a trusted communication path for delivery of the authorization code to the client system; the method comprising a server system receiving a message from the source system, the message comprising at least part of the resource identifier, and in response the server system storing the first code or the second code as an encrypted person identifier in association with the at least part of the resource identifier; wherein the client system is adapted to receive the authorization code via the trusted communication path and to receive the person identifier in order to generate using the encryption algorithm the encrypted person identifier based on the authorization code received by the client system and based on the person identifier received by the client system; the method comprising the server system receiving a request message from the client system, the request message comprising the encrypted person identifier as generated by the client system, the request message requesting the server system to provide the at least part of the resource identifier; and in response the server system transmitting the at least part of the resource identifier to the client system, wherein the client system is configured to gain access to the confidential information stored on the source system using the at least part of the resource identifier.

In another aspect the disclosure relates to a server system for enabling a client system to access confidential information stored at a source system, the client system being configured to access the confidential information using a resource identifier, the server system comprising a computer readable storage medium having at least part of a program embodied therewith; and, a computer readable storage medium having computer readable program code embodied therewith, and a processor, preferably a microprocessor, coupled to the computer readable storage medium, wherein responsive to executing the computer readable program code, the processor is configured to perform executable operations comprising one or more of the method steps, e.g. the method steps executed by a server system, as disclosed herein.

Once the source system, e.g. a system of a medical practitioner, such as a general practitioner, has output the authorization code, and/or has provided the authorization code to a user of the source system, this user (e.g., the general practitioner), may inform his patient of the authorization code as part of referring his patient to a medical specialist. The disclosed technology enables that the patient himself can decide which medical specialist to go to, at a later time, avoiding the need to determine this at the time the general practitioner makes the referral. Further, this way, the patient is in control over authorization: he can choose not to permit the medical specialist to request one of his medical records from the source system by not giving the authorization code to the specialist, or he can decide to not give the code until he meets the medical specialist in person. This way, the patient may decide whether or when to provide the authorization code. Without the authorization code, the client system or the medical specialist cannot generate the encrypted person identifier, nor obtain the resource identifier from the server system, nor request the confidential information from the source system. The patient thus remains fully in control of access to his records.

The technology is especially advantageous for employing unbound resource identifiers, such as unbound references disclosed in US 2014/0047513 A1, in situations wherein a general practitioner refers a patient to a medical specialist who is yet unknown, or who uses a yet unknown computer system. In an example, the general practitioner may refer his patient to an oncologist but may let the patient choose which oncologist he will visit. In another example, a general practitioner prescribes medication, wherein the patient is free to fill the prescription at any pharmacist. In such situations, it is useful for the oncologist or the pharmacist to have access to the patient's medication record as available at the source (i.e., at the general practitioner's system), but it is unsafe to simply publish the unbound resource identifier in a (widely accessible) server, or even to print the resource identifier on paper and give that to the patient as part of a referral letter or printed prescription note, because the resource identifier cannot be bound to a particular (user of a) client system up-front and thus may be misused by an attacker who obtains the resource identifier illegitimately.

If an unbound resource identifier were to be simply given to a patient so that he can give it to a medical specialist to his choosing, such an unbound resource identifier is exposed to the risk of being stolen and being used to request data from the source system (if not prevented by other security measures, such as client authentication that only permits medical professionals with a smartcard to request access, of course).

The disclosed technology enables that unbound resource identifiers can be more safely employed. After all, the technology does not require a patient to bring a directly usable unbound resource identifier to a medical professional, such as a specialist. Conveniently, the user only needs to bring the authorization code to the medical specialist. This authorization code will be useless for someone who finds or steals only a note or a letter with the authorization code on it. The authorization code on itself namely does not enable someone to obtain the resource identifier from the server system, since the patient's identifier must also be known as well as the encryption method in order to generate a correct encrypted person identifier that is needed to locate the resource identifier. The server system may employ additional access control mechanisms to ensure that only healthcare professionals may invoke operations on it, specifically to obtain a resource identifier using an encrypted person identifier, to provide defence in depth. Note also that a client may not request information from a source system directly using a code alone, since the source system may only allow requests using a resource identifier as it was stored in and obtained from the server system, in combination with the authorization code.

In addition, the disclosed technology provides improved confidentiality and privacy protection because no use is made of a centralized system that comprises confidential information. The server system namely does not store any confidential information that allow patient identification, such as social security numbers or other types of (national) identifiers for patients, that may be required in systems that do not make use of the approach described in this application. An attacker that unlawfully gains access to the server system may only find information that is completely unrelatable to individuals. Hence, even if sensitive information would be derivable from information stored in the server system, it cannot be related to a particular person. This provides "privacy by design", or "data protection by design" as prescribed by the EU general data protection regulation (GDPR). Further, because the authorization code, which acts as a secret key shared only between a source and a client system/recipient of an authorization, is not stored centrally in the server, an attacker who gains access to the central system has no use of the resource identifiers stored in this system, as this information can only be used in conjunction with the corresponding authorization code(s) to obtain confidential information from the source system.

An advantage of requiring the client system to provide the authorization code to the source system before the source system will provide access to the client system is that an additional authorization step at the source system may be performed before access is permitted and/or before the resource identifier is bound to the client system. As said, the resource identifier generated by the source system is stored in association with the authorization code at the source, but the authorization code is not stored in or known by the server. Hence, upon having received from the client system both the resource identifier and the authorization code, the method for the source system may comprise, and/or the source system may be configured for, determining that the received authorization code and resource identifier were indeed already stored in association with each other in the source system, and in response providing the client system access. This authorization step would rule out the possibility that someone has broken into the server system, obtained resource identifiers and has used these for requesting data from the source system without actually having obtained the authorization code from a patient.

An advantage of the source system, in response to receiving the request message from the client system, instructing the client system to provide the authorization code, is that it allows the authorization code to be transmitted from the client system to the source system over a secure connection between the source system and the client system, which secure connection may be established after (when) the source system has (first) received the request message from the client system. Mechanisms exist to ensure that a secure connection is established before sending a request; such mechanisms are employed in standard authentication and secure connection setup protocols like TLS and https.

In one example, the confidential information comprises medical data of the person, for example privacy sensitive information and/or patient information. The system can also be used outside healthcare, for the secure exchange of other types of (confidential) information. To illustrate, the confidential information may comprise a legal document of a law firm's client, which document is stored on a computer system of the law firm. The computer system of the law firm may then be understood to be the source system as described herein. Another example may be a police officer or a police department sharing a case file with another police department.

The resource identifier may enable the source system to identify and/or retrieve the confidential information, for example from a storage of the source system. It should be appreciated that at least a part of the resource identifier may not be interpretable by the client system, or in other words, may be "opaque" to the client system. The client system using the resource identifier for sending the request to access the confidential data may comprise the client system including the resource identifier in said request and/or the client system using the resource identifier to transmit the request to the source system.

The resource identifier may comprise at least one of an address of the source system, a pointer to the data, and information describing the data pointed to and policy information. The address of the source system may enable the client system to transmit messages to the source system or fetch data from it, for example using HTTP operations.

Policy information may be associated with each resource identifier at the source, and may be optionally exposed to client systems in or through the resource identifier. The policy information may be exposed to a client system through the resource identifier in the sense that the client system can use a read operation based on the resource identifier to obtain the policy information. An example would be the operation GET<URL>?view=policy. Policy information may define terms of use for the resource identifier or for the information pointed to by the resource identifier. The policy may define a role based access control scheme that may indicate that the resource identifier may be used only by a specific group of persons, for example by persons who practice a certain medical specialism, such as gynecology or internal medicine. In another example, the policy may indicate an expiration date, implying that the resource identifier may only be bound to or used within a certain time period. In yet another example, the policy may indicate what kind of further authorization steps are required before someone may bind or use the reference, for example that a PIN code is to be provided by someone who intends to use the resource identifier, and that (the user of) a client system must prove that it possesses a certain type of certified smartcard or public key certificate. In some embodiments, the authorization code may be usable as a PIN code, to be presented every time that a connection to the source is made, as a form of authentication; it may also be needed to present it only once, at binding time (a PIN may be unrelated to the authentication code). As another matter defined by policy, a medical specialist that wants to request a medical record of a patient may be required to authenticate himself or his client system using a certified personal healthcare smartcard that contains a certificate proving the specialist's name and specialty or role). There may also be policy constraints on the usage of information that is obtained through a resource identifier, or of the usage of the resource identifier, for example, restrictions on copying the confidential information or the resource identifier. As a concrete example, it may be that the policy dictates that copying the retrieved information is forbidden, and that the only way to pass a patient's information to another healthcare professional or healthcare organization, is through copying the resource identifier by invoking a method on the source system and passing a resulting (unique, new) resource identifier to this other healthcare professional or organization; this concrete example is a policy which is described in US 2014/0047513 A1.

It should thus be appreciated that one use of the resource identifier may comprise using the resource identifier to request access to confidential information, but that another use is to copy the resource identifier, in the sense of requesting a new resource identifier from the source system, the new resource identifier also being indicative of the data storage location at the source system wherein the confidential information are stored, yet the new resource identifier optionally being different from the (original) resource identifier. In an example, the resource identifier comprises a first URL that comprises the address of the source system as a domain name, an indication of the data storage location within the source system as a pathname, and a first random number. In this example, the new resource identifier may then be a second URL that comprises the same domain name and path name as the first URL, yet that comprises a second random number that is different from the first random number. Hence, the second URL may point to the same confidential information yet may be different and each unique. This allows the second URL to be bound to another client (key) than the first. Note that, in a specific embodiment, the second URL may not be passed to another healthcare professional or organization directly; instead, the second URL may be constructed using the method described in the present invention, where the client bound to the first URL requests the source to generate an authorization code and to register a new URL, in association with an encrypted person identifier, in the (known) central server, returning the authorization code to the client bound to the first URL, who can provide the authorization code to the healthcare professional or organization that he intends to authorize, or to the patient who may subsequently choose a healthcare professional or organization to authorize by providing the authorization key to that healthcare professional or organization. It is thus that the present invention is also applicable to the method of reference copying described in US 2014/0047513 A1, preventing that transitive authorization requires a healthcare professional to send or otherwise pass a large, bound or unbound URL to another healthcare professional, which would be very inconvenient in practice.

In embodiments, the method for the source system comprises, and/or the source system is configured for, storing the generated resource identifier in association with the encrypted person identifier and/or in association with the authorization code and/or in association with the person identifier and/or in association with the confidential information. These embodiments advantageously enable the source system to relate an incoming request comprising the resource identifier to the correct information.

The authorization code may comprise a one-time pad for the encryption method and may be regarded as a secret key. Hence, the resulting encrypted person identifier may be a one-time encrypted person identifier, for example in the sense that the encrypted person identifier is not associated with any other resource identifier generated by the source system or another source system, for example other resource identifier URLs generated for confidential information for the same person. These measures secure the anonymity of the person.

A trusted communication path may comprise a trusted person, e.g. a user of the source system or said person, who may be authorized to manage access to the confidential data, or both the trusted person and said person. The source system providing information, e.g. the authorization code or a part of a resource identifier mentioned below, to a trusted communication path may thus comprise the source system outputting the information so that a user of the source system can obtain the information and can select the further path for delivery of the information to the client system. The source system outputting the information for example comprises the source system printing the information, rendering the information on a display and/or loading the information onto an external memory. In an example, the user of the source system provides said information, e.g. said authorization code, to said person who can bring it to the client system himself. In another example, the trusted communication path includes electronic messaging, such as e-mail sent over a trusted email server, or an encrypted messaging system such as "Signal" (by Open Whisper Systems), and providing information to the trusted communication path may comprise electronically transmitting the information to said person.

In particular examples, providing information to a trusted path may comprise the following aspects:

the source system embedding the information in an electronically delivered message comprising a referral letter, a prescription, or another electronic message sent and delivered to a healthcare professional that is involved with treatment of the person;

or the source system presenting the information to a doctor who operates the source system as part of the (user) interface that the doctor operates, where the doctor can write the code on a message that is hand-delivered to a person that operates a client system that is to retrieve the resource identifier and the personal identifier, the message for example comprising a paper card, a printed or handwritten prescription, or a (handwritten or printed) referral letter, or any other message that is given to the patient or to a second healthcare professional as part of the process of treating the patient, where the patient or the second healthcare professional should ensure that the authorization code, together with or as part of the message, is delivered to the healthcare professional or healthcare organization that is supposed to treat the patient further and that acts as the client system of claim 1; with the electronic or handwritten message preferably also containing the web address (URL) of the server process that contains the resource identifier associated with the encrypted person identifier of claim 1, e.g., verwijscode.nl or prescriptioncode.net.

The encryption algorithm may comprise an exclusive-or operation on the person identifier and the authorization code, for example the operation "person identifier XOR authorization code". It should be appreciated that the encryption method may be any method or (one-way) function, also for example as a keyed-hash based message authentication code (HMAC) or signature algorithm. It should be appreciated that he encryption algorithm used by the source system and the encryption algorithm used by the client system may be the same. The encrypted person identifier may comprise a one time pseudonym.

In embodiments, the resource identifier may comprise a URL generated by the source system, wherein the URL may comprise a FQDN of the URL that may point to the source system and wherein the URL may comprise a pathname that may indicate a specific resource (e.g., patient record) stored at the data storage location at the source system. It should be appreciated that where, for clarity of exposition, we use the term URL, the same applies to other embodiments of a resource identifier in the general sense.

In one embodiment, the resource identifier may comprise an opaque identifier (not location based) such as used in known peer-to-peer (p2p) systems, for example hashes of filenames that can be mapped on multiple internet addresses (that contain [copies of] the files) by the p2p system.

In embodiments, the method for the source system comprises, and/or a request handling module of the source system is configured for, determining that at least part of the received resource identifier (e.g., pathname) from the client system is identical to resource identifier generated earlier by the source system, and, subsequently further process the request. The source system may only accept a request if the request comprises a resource identifier generated earlier by the source system itself.

In embodiments, the method for the source system comprises, and/or the source system is configured for, upon receiving the request for access to the confidential information or upon receiving the authorization code from the client system, binding the client system or a user of the client system to the resource identifier, for example by storing an identifier or a key of the client system and/or an identifier of the user in association with the resource identifier, which in typical embodiments takes the form of a URL. As a result, the resource identifier may from that point onwards only be usable by said (user of the) client system, and not by any other (user of the) client system.

In embodiments, the authorization code may be provided by the client system to the source system by the client system by including the authorization code in the request to access the confidential information, for example by including the authorization code in the URL in a predefined location of the pathname of the URL to complete the URL (if the authorization code was removed from the URL earlier, by the source, before storing the URL in the central server), and/or by including it in the request message, and/or by the client system receiving, after transmitting the request to access the confidential information to the source system, an instruction from the source system to provide the authorization code and in response the client system providing the authorization code to the source system.

In one embodiment, the message from the source system to the server system instructs the server system to store the second code as the encrypted person identifier in association with the at least part of the resource identifier and the source system provides the first code as the authorization code to the trusted communication path. Thus in one embodiment the method for the server system comprises in response to receiving the message from the source system, the message comprising the at least part of the resource identifier, storing the second code as the encrypted person identifier in association with the at least part of the resource identifier.

In an example of this embodiment, the encryption algorithm is an XOR-operation and if the encrypted person identifier is denoted by EID, the person identifier by ID, the authorization code by AC, and the resource identifier by URL, an example of part of the method could be (schematically):

i) source system: generating URL
ii) source system: generating AC
iii) source system: AC XOR ID[] EID
iv) source system: transmitting URL and EID to server system
v) source system: providing AC via trusted communication path to client system
vi) client system: receiving ID and AC
vii) client system: AC XOR ID[] EID
viii) client system: using EID to retrieve URL from server system.

In another example of this embodiment, the XOR operation may be replaced by a one-way cryptographic operation [or function] that takes AC as a key to encrypt ID to generate EID.

In one embodiment, the encryption algorithm is a reversible encryption algorithm such as said XOR operation, and the message from the source system to the server system instructs the server system to store the first code as the encrypted person identifier in association with the at least part of the resource identifier. In this embodiment source system provides the second code as the authorization code to the trusted communication path. This embodiment is advantageous, because it allows the server system to instruct the source system to use a specific encrypted person identifier, or the source system to request an encrypted person identifier that the client system can use to generate an AC. Preferably said specific encrypted person identifier is not yet stored in association with a resource identifier in the server system. This embodiment may ensure that the server system only receives a unique encrypted person identifier that is not currently in use. In one particular example, the source system thus receives the first code from the server system. The server system may thus (be configured to) determine an encrypted person identifier that is not yet stored in the server system and transmit it to the source system.

In an example of this embodiment, the reversible encryption algorithm is an XOR-operation and if the encrypted person identifier is denoted by EID, the person identifier by ID, the authorization code by AC, and the resource identifier by URL, an example of part of the method could be (schematically):

i) source system: generating URL
ii) server system: transmitting EID to source system
iii) source system: IED XOR ID[] AC
iv) source system: transmitting URL and EID to server system
v) source system: providing AC via trusted communication path to client system
vi) client system: receiving ID and AC
vii) client system: AC XOR ID[] EID
viii) client system: using EID to retrieve URL from server system.

In one embodiment, the message from the source system to the server system comprises a first part of the resource identifier. In this embodiment the method further comprises the source system providing a second part of the resource identifier to a second trusted communication path for delivery to the client system, wherein the client system is adapted to receive the second part of the resource identifier via the second trusted communication path and to use the first part of the resource identifier and the second part of the resource identifier to construct the resource identifier for sending the request to the source system. This embodiment thus enables that part of the resource identifier is used as a token that must be used to complete a resource identifier. Advantageously this token may be delivered to the client system via alternative trusted communication paths, which increases security of the confidential information. The second part of the resource identifier may comprise the authorization code or an encoded version thereof.

Thus, the second part may be the authorization code, which code the source system provides to said trusted communication path for delivery to the client system. Only once the client system has received this code, it can complete the first part of the resource identifier obtained from the server system and use the completed version of the resource identifier, or the URL described e.g. in step 214b of FIG. 2B, to send the request for the confidential information to the source system.

In some concrete embodiments of the above examples, a person identifier may be shortened first, e.g., by removing the first digits or characters, and/or the last digits or characters of the ID, so that the length of the person identifier is equal to the length of the authorization code, if there exists a requirement for keeping the length of the authorization code small, for example because a (handwritten) authorization code needs fit in a small area on a prescription letter; it may be appreciated that such permutations can be part of the encryption method, whether the encryption operation is symmetric or not.

In embodiments, the method for the source system comprises optionally in response to receiving the authorization code from the client system, the source system instructing the server system to erase the encrypted person identifier and the associated resource identifier from the server system. Optionally the source system instructs the server system at a point of time that is unrelated to a point of time at which the source system receives, or is expected to receive, the request message from the client system and/or that is unrelated to a point of time at which the server system receives, or is expected to receive, a request from the client system. This prevents potential indirect information leakage through timing attacks.

Alternatively or additionally, an expiration time may be stored at the server system in association with the resource identifier and the encrypted person identifier. This may avoid that stale resource identifiers linger in the server system if they are not used or requested. These embodiments conveniently enable the source system to control which resource identifier is stored at the server system, and for how long, and at what given time the resource identifier may or must be removed.

In embodiments, the method for the server system comprises the server system receiving from the source system an instruction to erase the stored encrypted person identifier and the associated resource identifier from the server system; and in response the server system erasing the encrypted person identifier and the associated resource identifier from the registry.

In embodiments, the method for the source system comprises the source system generating a fake resource identifier and optionally a fake person identifier; and the source system transmitting a second message to the server system, the second message comprising the fake resource identifier and optionally the fake person identifier, the second message instructing the server system to store the fake resource identifier optionally in association with the fake identifier; the source system receiving from a second client system a second request to access data, determining that the fake resource identifier was used by the second client system for sending the second request to the source system, e.g. by determining that the second request comprises the fake resource identifier; and in response flagging the second client system.

These embodiments are advantageous, because they enable to identify parties as potentially malicious, particularly attacks who gained access to the central server and may have guessed the person identifiers associated with the resource identifiers, e.g., through an external means such as knowledge about when a given patient went to his general practitioner. In these embodiments, the at least one fake identifier may be generatable by performing the encryption method using a dummy authorization code. Preferably, the dummy authorization code comprises at least two, more preferably at least three, most preferably at least four, symbols that are not comprised in the authorization code. This namely may prevent that a client system is undeservedly flagged when for example a user of the client system makes one typographic error when inputting the authorization code into the client system. If the erroneous authorization code is identical to the dummy authorization code mentioned above, the client system would obtain, using the encryption algorithm, an identifier that is identical to a fake identifier, as a result of which the client system would be undeservedly flagged as potentially malicious. (Otherwise, one would typically not hit an encrypted ID).

In embodiments, the method for the client system comprises transmitting a message to the source system, the message comprising new confidential information of the person and optionally requesting the source system or the author/healthcare professional responsible for the source record to store the new confidential information in association with the person identifier. Preferably the new confidential information is transmitted over the secured connection via which the authorization code was also originally provided to the source system. The method for the source may comprise, and/or the source system is configured for, receiving and storing the new confidential information in association with the person identifier, possibly notifying the source system's owner of this new information. These embodiments enable that medical records stored at the source system are kept up to date. In an example, a pharmacist uses the client system to inform the source system that he has filled a prescription and provided medication to a patient. This information may be added to the medical records of the patient as stored at the source system. In alternative embodiments, the information may be directly written or appended to the source records, as an "update" of the source record.

In embodiments, the method for the server system comprises the server system transmitting a notification message to the source system, the notification message notifying the source system that a request message comprising the encrypted person identifier has been received from a client system; and/or the notification message notifying the source system that the resource identifier has been transmitted to a client system. These embodiments are advantageous because they enable a general practitioner of a patient to monitor the status of the resource identifier he has provided to the server system, and to monitor whether some party has attempted to obtain the resource identifier.

In one distinct aspect, this disclosure relates to a computer program product comprising instructions to cause the source system disclosed herein to execute one or more of the methods for the source system disclosed herein and/or instructions to cause the server system disclosed herein to execute one or more of the methods for the server system disclosed herein and/or instructions to cause the client system disclosed herein to execute one or more of the methods for the server system disclosed herein.

Yet another aspect of this disclosure relates to a computer-readable medium having stored thereon said computer program product.

As will be appreciated by one skilled in the art, aspects of the present invention may be embodied as a system, a method or a computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Functions described in this disclosure may be implemented as an algorithm executed by a processor/microprocessor of a computer. Furthermore, aspects of the present invention may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium may include, but are not limited to, the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present invention, a computer readable storage medium may be any tangible medium that can contain, or store, a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber, cable, RF, etc., or any suitable combination of the foregoing. Computer program code for carrying out operations for aspects of the present invention may be written in any combination of one or more programming languages, including an object oriented programming language such as Java(™), Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the present invention. It will be understood that each block of the flowchart illustrations and/or block diagrams, and combinations of blocks in the flowchart illustrations and/or block diagrams, can be implemented by computer program instructions. These computer program instructions may be provided to a processor, in particular a microprocessor or a central processing unit (CPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

In one aspect, embodiments of the present invention may relate to a computer-implemented method for providing a client system access to confidential information of a person stored at a source system.

Moreover, a computer program for carrying out the methods described herein, as well as a non-transitory computer readable storage-medium storing the computer program are provided. A computer program may, for example, be downloaded (updated) to the existing source system and/or server system and/or client system or be stored upon manufacturing of these systems.

Embodiments of the present invention will be further illustrated with reference to the attached drawings, which schematically will show embodiments according to the invention. It will be understood that the present invention is not in any way restricted to these specific embodiments.

BRIEF DESCRIPTION OF THE DRAWINGS

Aspects of this disclosure will be explained in greater detail by reference to exemplary embodiments shown in the drawings, in which:

FIGS. 3A and 3B illustrate, according to one embodiment, data stored at the source system and server system respectively;

DETAILED FIGURE DESCRIPTION

Figure 1:
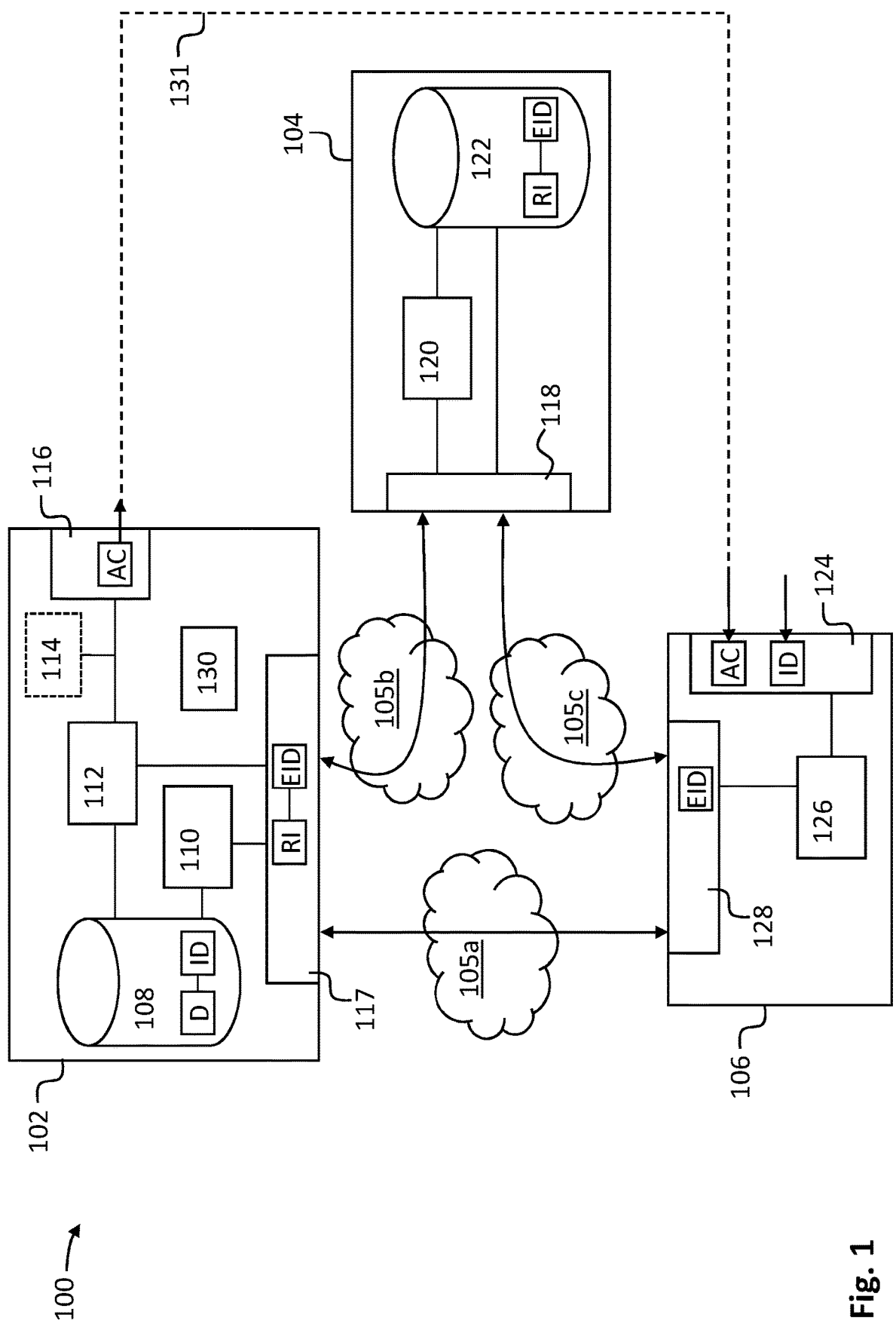
FIG. 1 illustrates a system according to one embodiment of the invention.

FIG. 1 shows a system 100 according to one embodiment of the invention. The system comprises a source system 102 according to one embodiment of the invention, a server system 104 according to one embodiment of the invention and a client system 106 according to one embodiment of the invention. The system 100 may comprise numerous source systems 102, numerous server systems 104 and numerous client systems 106 as described herein.

In one embodiment, the source system 102 comprises a communication module 117 that is configured to connect to a network 105a and/or to network 105b. In one embodiment, the client system 106 comprises a communication module 128 that is configured to connect to network 105a and/or to network 105c. In one embodiment, the server system 104 comprises a communication module 118 that is configured to connect to network 105b and/or to network 105c. Hence, the systems 102, 104, 106 may be able to communicate with each other via the respective networks 105.

The networks 105a, 105b and 105c may be different networks or may be the same network, e.g. the internet. Alternatively, two of the three networks 105a, 105b and 105c, for example network 105b and 105c, may be the same network, whereas the third network, for example network 105a, is a separate network. Each of the networks 105a, 105b and 105c may be a wide area network, such as the internet, but may also be a local area network. In one particular example, network 105a is a local computer network of a hospital and networks 105b and 105c are the same network being the internet. The networks may comprise (virtual) private networks (VPNs).

It should be appreciated that each of the communication modules 117, 118, 128 may be configured to establish an end-to-end authenticated connection and/or private connection, for example with a communication module of another system. Such connections may be based on a cryptographic protocol, examples of which are the Transport Layer Security (TLS) and the Secure Sockets Layer (SSL) protocol known in the art. Hence, information may be communicated between the source system 102, client system 106 and the server system 104 securely.

In one embodiment, the source system 102 comprises a storage 108 and may be configured to store confidential information of a person in the storage 108. The person is identified by a person identifier and the source system may be configured to store the confidential information in association with the person identifier. In the drawings, the confidential information is indicated by the letter "D" and the person identifier with the letters "ID". The person may be a natural person, but may also in some cases be an organization or a legal entity, such as a company, which organization or legal entity owns the confidential information or is entitled to control access to the confidential information. The person may also be a representative of such organization or legal entity. The source system can be used to control access to data which is confidential, such as intellectual property.

The person may be the data subject, for example in case the confidential information comprises privacy sensitive information about the person. The person identifier may comprise at least one of the person's name, date of birth and social security number. The person identifier may be a globally unique and/or National identifier such as a BSN (Burgerservicenumber) in Holland, but it may also be a sectoral number, such as a healthcare ID, or a (health) insurance number, a driver's license number, or even a number known only to the source and the patient (and, ultimately, the client system who needs this identifier in combination with the authorization code to compose EID). Since the person may be a company, the person identifier may also be a company identifier.

The person identifier may also be a postal code associated with the person combined with a date of birth of the person (e.g. these two elements concatenated in a predefined order)—or a combination of other information associated with the person or source record, e.g. encoded as character strings, such as a combination of postal code and the person's surname, or a combination of postal code, a house number and a year of birth. Although the outcome of such a combination is not guaranteed to be unique—as the social security/BSN in the Netherlands is—it can still be used as person identifier, since the operation <postal code+date of birth> XOR <authorization code (AC)> will yield a unique Encrypted Identifier (EID) that is different from the Encrypted Identifier that would result from the same combination of postal code+date of birth being XOR'ed with another AC. It is easily understood that the probability that two identical AC's are respectively used for two identical combinations of postal code+date of birth, can be made negligibly low, e.g. by using random number for the AC's. The goal of the person identifier may be understood as to allow generation of a one-time, unique, unguessable encrypted identifier (EID) that is to be stored in the server system, while allowing the client system to compose this EID using the AC and the person identifier. In this context, person identifier can be replaced by a combination of a postal code and a date of birth, or another combination of known attributes of a given person/patient. It should be appreciated that such a replacement of a person identifier is useful when a person does not have a social security number/BSN nor another known unique person identifier (but does have an address and a known date of birth, for example).

In one particular example, the person is a patient, the person identifier is a patient identifier and the confidential information comprises at least one medical record of the patient. The person identifier may be a unique patient identifier within non-universal patient identifier schemes; as long as the healthcare professional at the client system can figure out what the identifier is based on external information; an example is by having the patient present an authentication document such as a passport, driver's license or insurance card.

In one embodiment, the source system 102 is associated with a first doctor, such as a general practitioner of the patient, and/or with a first medical organization, who acts as a data controller and/or is responsible for the data, including for protecting the data, such as a GP practice or a hospital or a cooperative of several general practitioners. The first doctor/medical organization may keep at least one confidential medical record of the patient.

In one embodiment, the source system 102 is owned by the person whose confidential information is to be transmitted to the client system. The person may have installed the source system 102 at his home (or, when the person is a legal entity such as a company, at this company; or at any other location, physical or virtual), and may thus be the user of the source system 102.

The source system 102 may comprise a resource identifier generator 110 that is configured to generate a resource identifier, wherein the resource identifier is indicative of a data storage location at the source system. The data storage location may be a memory area in the storage 108. In the drawings, the resource identifier is indicated by the letters "RI". The resource identifier may comprise information that is required for requesting the source system 102 access to the confidential information. The resource identifier may comprise at least one of an address of the source system 102, such as a Domain Naming System (DNS) name, and a (path)name indicating the data pointed to, and additional information such as but not limited to policy information that is described below. It should be understood that it may be impossible for a particular entity, such as a client system 106, to request the confidential information from the source system 102 if the entity does not have the resource identifier to the data. The source system 102 may be the only entity that can generate such resource identifier to the confidential information. The resource identifier may be formatted as a character string, such as a URL. The resource identifier generator 110 may be operatively connected to the storage 108.

The resource identifier may, typically, as part of the pathname [or as the part that indicates a specific resource at the source], comprise type information describing how information obtained from or written to a source record may be represented electronically; a random number to ensure the reference is unique; policy information that describes the type of actions that may take place with the reference (e.g., reading or writing the record pointed to, or copying the reference, effectively creating a new, unique reference pointing to the same record as the original one); and security/authorization information that indicates to the recipient of the reference how it can authenticate when connecting to the source system in order to dereference the reference and invoke an operation on the reference. Further, a reference may contain a unique identifier of the patient (including the encrypted person identifier EID described below, which acts as a pseudonym), so as to allow a client (system) that receives a URL to determine the person that the resource identifier belongs to, solely by analyzing the content of the resource identifier, such as a social security number. Resource identifier in practice may take the form of a URL, with the URL's pathname containing the record identifier, record type information, random number, policy, and authorization information and possibly patient identifier, although it should be appreciated that resource identifiers may also be represented in other ways than the well-known URL (http/https) character string representation.

In one embodiment, the source system 102 is configured to store the generated resource identifier in storage 108 in association with the person identifier and/or with the confidential information. This enables that the source system 102, upon receiving the resource identifier from the client system 106, will be able to retrieve the confidential information and/or the person identifier on the basis of the resource identifier received from the client system 106.

In one embodiment, the source system 102 comprises an encryption module 112 that is configured to generate an encrypted person identifier based on the person identifier and based on an authorization code, e.g. configured to encrypt the person identifier using the encryption algorithm on the basis of an authorization code. In the drawings, the encrypted person identifier is indicated by the letters "EID". The encryption algorithm may comprise inputting the person identifier and the authorization code into a one-way function, wherein the one-way function outputs the encrypted person identifier. Alternatively or additionally, the encryption method comprises performing an exclusive-or operation: person identifier XOR authorization code. Another function may be an (encrypted) HMAC taking an authorization code as an encryption key as input to generate a cryptographic signature over a personal ID (or vice versa). Hence, it may be impossible to derive the person identifier from the encrypted person identifier without knowing the authorization code; it should be appreciated that an authorization code acts as (secret) encryption key.

In the drawings the authorization code is indicated by the letters "AC". The authorization code may be a one-time pad to be used for encryption. In an example, the authorization code is a random number, which may be cryptographically generated. Optionally, the source system 102 comprises a random key generator 114, that is configured to generate the authorization code, such as a random authorization code, for example a random number.

In one embodiment, the source system 102 comprises an interface 116, for example located at the first doctor and/or at the first medical organization, that is configured to provide the authorization code to a trusted communication path for delivery to the client system, which providing may include outputting the authorization code. The interface 116 may be configured to provide the authorization code to a user of the source system 102 and/or to a device (not shown) connected to the source system 102, in particular connected to interface 116. Herein, said user and device may thus be part of said trusted communication path. In general, the interface 116 may be configured to enable information exchange between a user of the source system 102, for example the first doctor mentioned above or a patient, and the source system 102. The interface 116 may be a user interface and for example comprises a display. The user interface 116 may be configured to render the authorization code visible on the display in order to reveal the authorization code to a user of the source system 102. In another example, the interface 116 comprises an output for storing the authorization code onto an external storage device, such as a USB stick or a smartcard. The interface 116 may also comprise a printer for printing the authorization code, or a representation of the authorization code, such as a barcode onto a medium, such as a piece of paper, a sticker, or on a credit-card sized medium for storage in a wallet; it may also be that the system 102 provides an electronic interface that allows a (sub) system to retrieve the code, so this (sub)system, which can be connected to or be part of the source system 102, may include the code in a prescription or in a referral letter, in paper or in an electronic form.

Once the user of the source system 102 has obtained the authorization code, he may provide it to the person whose person identifier is stored in storage 108. Of course, the user of the source system 102 may also provide the authorization code to a representative of the person, or to someone who is authorized by the person to receive the authorization code.

In one particular example, the interface 116 provides the authorization code to a general practitioner who in turn informs his patient of the authorization code. The general practitioner may conveniently hand over a piece of paper, such as a prescription or a referral letter, with the authorization code printed or written on it. In another example, the general practitioner simply tells the authorization code to his patient.

After the authorization code has been output by the source system, the output authorization code may be transmitted to the client system out-of-band. In an example, the person brings the authorization code in person to client system 106 as indicated by the dotted line 131. In yet another example, a user of the source system, e.g. the GP, tells a user of the client system, e.g. a doctor or a nurse at an emergency ward at the hospital, the authorization code over the phone. The user of the client system may then immediately input the authorization code into the client system 106 via interface 124. The trusted communication path may thus include an external, (secure) means of communication.

In a particular example, the user of the source system is not the owner of the source system but a person, optionally remote from the source system, who is authorized to use the source system. The person may be authorized using methods describe in US20140047513A1. This authorized person may instruct, e.g. via a remote interface, the source system to generate and/or retrieve the first code and to generate the second code using the encryption algorithm. In response, the source system may carry out the requested steps and send the second or first code as authorization code to the user of the source system, who in turn can then provide the authorization code to another party via the trusted communication path, e.g. by telling the authorization code over the phone to said another party.

In one embodiment, the source system 102 comprises a communication module 117 that is configured to transmit a message to the server system 104. The message may comprise the resource identifier and the encrypted person identifier. Further, the message may instruct the server system 104 to store the encrypted person identifier in association with the resource identifier. The source system 102 may be configured to associate the encrypted person identifier with the resource identifier and store the encrypted person identifier in association with the resource identifier, and optionally in association with the confidential information and/or with the person identifier, in storage 108. The source system 102 may be configured to add the encrypted person identifier to the resource identifier. In one particular example, the resource identifier generator 110 generates the resource identifier, wherein the resource identifier comprises the encrypted person identifier.

In one embodiment, the communication module 117 is configured to receive from the client system 106 a request to access the confidential information. This request may have been generated based on the resource identifier and/or comprise the resource identifier of the confidential information. How the client system 106 may have obtained this resource identifier will be explained below.

In one embodiment, the source system 102 comprises a request handling module 130 that is configured to provide the client system 106 access to the confidential information on the basis of the received request message, in a particular example on the basis of the resource identifier comprised in the received request message, by transmitting at least part of the confidential information to the client system 106. In one example, the request handling module 130 is configured to determine that the received resource identifier is identical to the resource identifier generated earlier by the source system 102 and to, on the basis of this determination, provide the client system 102 access.

In a further embodiment, the request handling module 130 is configured to receive from the client system 106 not only the resource identifier but also the authorization code obtained by the client system and to provide the client system 102 access to the confidential information on the basis of the received request message and on the basis of the authorization code received from the client system. In one particular example, the request handling module may be configured to determine that the received authorization code and the resource identifier received from the client system 106 were already, prior to receiving these from the client system 106, stored in association with each other in the source system 102, and to in response provide the client system 106 access.

In yet a further embodiment, the request handling module 130 is configured to, in response to receiving said request from the client system 106, instruct the client system 106 to provide the authorization code (e.g., using a "PIN" type dialog and/or a challenge-response where the client must present either the authorization code in full, or prove to have possession of the authorization code known at source system 102).

The source system 102 may be further configured to instruct the server system 104 to erase the encrypted person identifier and the associated resource identifier from a registry 122 in the server system 104, within some bounded interval of time. Herewith the user of the source system 102 remains in control regarding the resource identifier it has generated.

In one embodiment, the resource identifier generator 110 in source system 102 is configured to generate fake resource identifier and a fake encrypted person identifier. In this embodiment, the communication module 117 may be configured to transmit a second request message to the server system 104, the second request message comprising the fake resource identifier and/or the fake identifier, the second request message instructing the server system 104 to store the fake resource identifier optionally in association with the fake identifier. The request handling module 130 may then be configured to receive from a second client system a request to access data, the request comprising the fake resource identifier and/or the fake person identifier and to flag the second access client system on the basis of the received fake resource identifier and/or on the basis of the fake person identifier. This embodiment allows to identify a party as potentially malicious, e.g. a party that has unlawfully obtained resource identifier and/or identifiers from the server system 104.

Conveniently, the server system 104 may be configured to not be able to distinguish between real and fake information. The server system 104 preferably does not comprise information that indicates whether resource identifier and/or encrypted person identifiers stored at the server system are fake or real, so that anyone who unlawfully gains access to the server system 104 cannot distinguish between fake and real information.

The server system 104 may comprise one or more servers. The server system 104 may be publicly available and/or publicly reachable. In one example, the server system 104 is configured to host a website, the website being publicly reachable for a web browser, for example a web browser that is installed on client system 106 and/or on source system 102. It should be recognized that the server system can have or be known by a short, well-known and easy to remember internet domain name such as prescriptioncode.org, or referralservice.com, so that the system is easy to use in practice.

In one embodiment, the server system 104 comprises a communication module 118 that is configured to receive from the source system 102 the message that comprises the encrypted person identifier and the resource identifier described above.

The server system 104 may further comprise a registry 122 and the server system 104 may be configured to store the encrypted person identifier in association with the resource identifier in said registry 122.

Furthermore, in one embodiment, the server system 104 comprises a communication module 118 that is configured to receive from the client system a request message, the request message comprising the encrypted person identifier. How the client system may have obtained the encrypted person identifier will be explained below.

Also, the server system 104 may comprise a request handling module 120 that is configured to, on the basis of the encrypted person identifier received from the client system and on the basis of the encrypted person identifier received from the source system, transmit the resource identifier to the client system. In an example, the request handling module 120 is configured to determine that the encrypted person identifier received from the client system 106 is related to, e.g. identical to, the encrypted person identifier received from the source system 102 and stored in association with the resource identifier and, in response, provide the resource identifier to client system 106. The server system 104 can thus provide a client system access to resource identifier.

Conveniently, no information is stored in the registry 122 that is relatable to a person. The registry 122 namely does not comprise any actual person identifiers, which is beneficial for security and privacy reasons as explained above. Also, strict laws relating to storage of personally identifiable information including person identifiers do not apply, which eases compliance issues and improves the ease of implementation of such registry 122.

In one embodiment, the request handling module 120 is configured to transmit a notification message to the source system, the notification message notifying the source system that the request message comprising the encrypted person identifier has been received from the client system 106 and/or the notification message notifying the source system 102 that the resource identifier has been transmitted to the client system 106.

In one embodiment, the server system 104 is configured to receive from the source system 102 an instruction to erase the stored encrypted person identifier and the associated resource identifier from the registry 122 of the server system; and to, in response, erase the encrypted person identifier and the associated resource identifier from the registry 122.

The client system 106 may be associated with a second doctor, for example a medical specialist, and/or with a second medical organization, such as a ward of a hospital, e.g., an emergency ward. The client system may be configured to access the confidential information using the server system as described herein. It should be appreciated, in the context of this disclosure, that a first/second doctor also includes a delegate of the first/second doctor, such as an assistant of the first/second doctor. In an example, the first doctor has referred a patient to a medical specialism, for example to oncology (not to any oncologist in particular), and the second doctor practices this medical specialism. In yet another example, the first doctor has prescribed medication for his patient and the second doctor is a pharmacist that needs to access a medical record of the patient before he can provide the medication to the patient.

In one embodiment, the client system 106 comprises an interface 124 that is configured to obtain, e.g. receive, the authorization code and the person identifier. The authorization code may have been output by interface 116 of the source system 102. The interface 124 may be located at the second doctor mentioned above. The (client) interface may, for example, be a stand-alone computer program or a program written in javascript that is contained in a web page that runs in a web browser. As explained, the trusted communication path 131 may comprise a person who is provided the authorization code via interface 116 of the source system 102, which person may bring the authorization code in person to the client system 106. The interface 124 may comprise a reader that is configured to read machine-readable information representative of the authorization code. In an example, the interface 124 comprises a barcode scanner. Additionally or alternatively, the interface 124 may comprise a keyboard, mouse, touch-sensitive surface, e.g. a touch sensitive display, via which a user of the client system 106 can input the authorization code into client system 106. The client system may comprise a program installed on a doctor's computer or run in a web browser, e.g., as javascript client code.

The person identifier may be obtained by the client system similarly as the authorization code. The user of the client system 106, for example the second doctor mentioned above, may ask the person who arrives at the client system 106, in particular at the interface 124, to provide an identification document comprising the person identifier, for example a passport comprising the person's social security number. The disclosed technologies thus compel the second doctor to ask a patient in front of him to show identification, which is advantageous because identification in healthcare is important to reduce the risk of fraud and/or medical errors, such as medication errors. The person identifier may be a driver's license or healthcare insurance identifier in cases a patient has no National ID (e.g., in case of a refugee), or in countries where a National ID may not be used in healthcare, or is not obligatory.

In one embodiment, the client system 106 comprises an encryption module 126 that is configured to use an encryption algorithm for generating the encrypted person identifier based on the person identifier and based on the authorization code obtained via interface 124. It should be appreciated that the encryption method used by encryption module 126 may be the same as the encryption method used by encryption module 112. The encrypted person identifier generated by the encryption module 126 may thus be the same as the encrypted person identifier generated by the encryption module 112. In an example the encryption module is embodied as a computer program product installed on a computer (not shown) of the client system 106.

In one embodiment, the client system 106 comprises a communication module 128 that is configured to transmit a request message to the server system 104. The request message may comprise the encrypted person identifier as encrypted by the client system 106, in particular by the encryption module 126. The request message may request the server system 104 to provide the resource identifier which the server system may have stored as described above.

In one embodiment, the communication module 128 is configured to receive the resource identifier from the server system 104.

In one embodiment, the communication module 128 is configured to transmit a request message to the source system 102, the request message requesting the source system 102 to provide the confidential information on the basis of the resource identifier. Understandably, the request message may comprise the resource identifier provided by the server system 104.

In one embodiment, the client system 106 is configured to gain access to the confidential information by receiving at least part of the confidential information from the source system 102.

In one embodiment, the client system is configured to provide the obtained authorization code to the source system. In one example, the client system is configured to include the authorization code in the request message that is transmitted to the source system 102.

In one embodiment, the client system 106 is configured to receive from the source system an instruction to provide the authorization code to the source system and to, in response, provide the authorization code to the source system or to return a response in response to a challenge to prove it has access to the authorization code.

In one embodiment, the client system is configured to transmit an message to the source system, the message comprising new confidential information and optionally the message requesting the source system or the doctor using the source system and responsible for its content to store the new confidential information in association with the person identifier or to otherwise update the confidential information. Preferably, new confidential information relating to the person may only be stored upon approval of the user of the source system 102, e.g. upon approval of the general practitioner of the person. In this manner, the general practitioner may stay in control of the medical records of his patient.

Figure 2A:
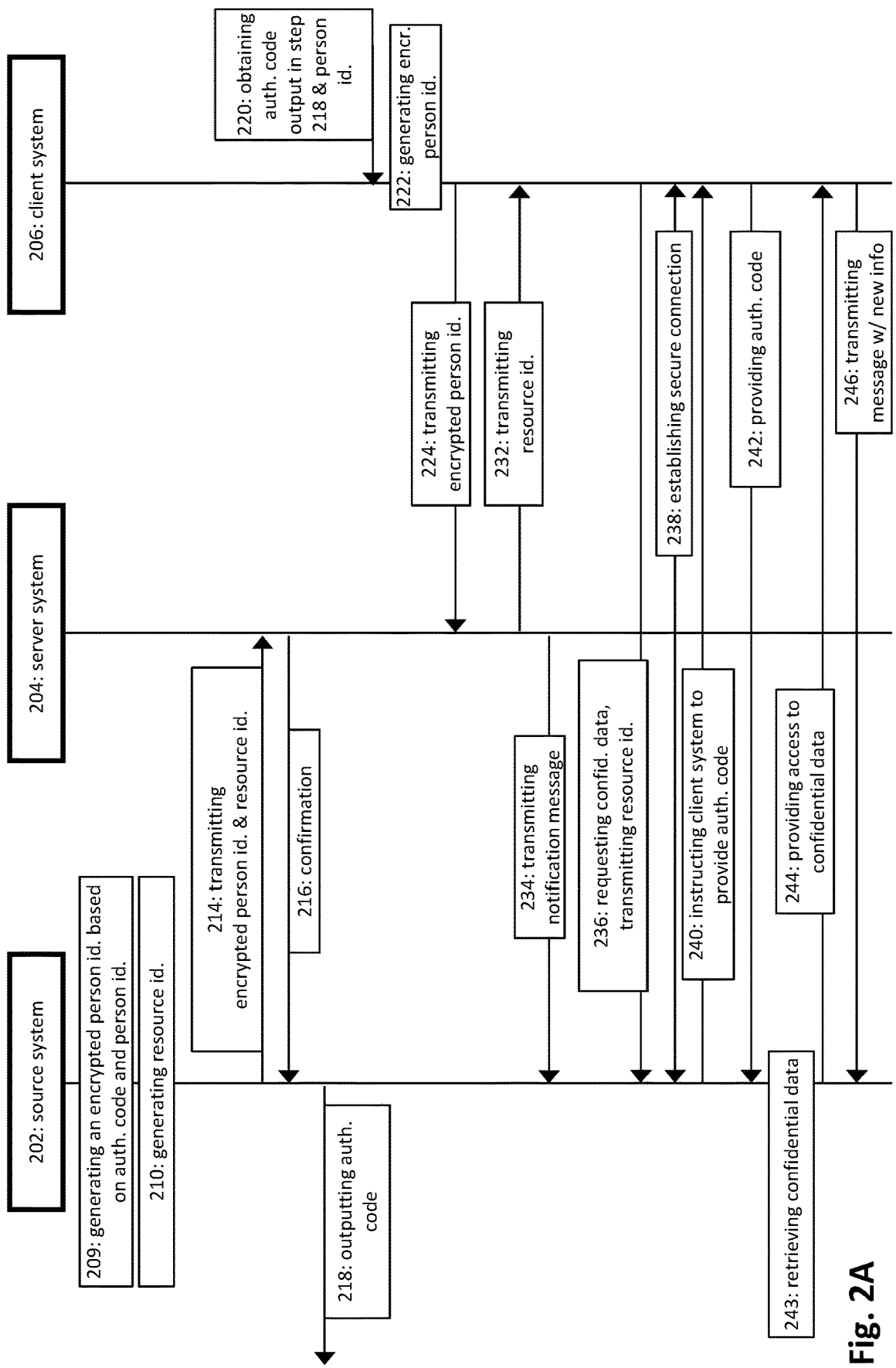
FIGS. 2A and 2B are flow charts illustrating steps of methods according to embodiments of the invention.

FIG. 2A is a flow diagram of a method according to one embodiment of the invention, the method being performed by a system according to one embodiment of the invention, the system comprising a source system 202, a server system 204 and a client system 206 according to respective embodiments of the invention.

Step 209 comprises using an encryption algorithm for generating an encrypted person identifier based on an authorization code and on a person identifier. Step 210 comprises generating the resource identifier. Then, the source system 202 transmits a request message 214 to server system 204, wherein the message comprises the resource identifier and the encrypted person identifier. Message 214 instructs the server system 204 to store the encrypted person identifier in association with the resource identifier. The server system receives message 214 and stores the encrypted person identifier in association with the resource identifier. Optionally the server system 204 transmits a message 216 to the source system 202, the message 216 comprising a confirmation that the server system 204 has stored the resource identifier and associated encrypted person identifier.

Further, the source system may output the authorization code in step 218. One embodiment comprises providing the authorization code to a user of the source system 202 and/or to the person whose person identifier is stored in the source system and/or to a device connected to the source system 202.

Step 220 comprises obtaining the authorization code and the person identifier. The authorization code obtained in step 220 may be the authorization code that is output in step 218. Step 222 comprises using an encryption algorithm for encrypting the person identifier on the basis of the authorization code. Once the encrypted person identifier has been generated, the client system 206 may transmit a request message 224 to the server system. The request message 224 may comprise the encrypted person identifier as encrypted by the client system 206. Further, the request message may request the server system to provide resource identifier received in step 214. The server system 204 receives message 224, and transmits message 232 to the client system 206 on the basis of the encrypted person identifier received from the client system in message 224 and on the basis of the encrypted person identifier received from the source system in message 214. Message 232 may comprise the resource identifier and may be received by the client system 206.

Optionally, server system 204 transmits a notification message 234 to the source system, wherein the message 234 notifies the source system 202 that the server system will transmit or is transmitting or has transmitted message 232 comprising the resource identifier to the client system 206. Understandably, the source system 202 and/or the server system 204 may keep record of how many times the resource identifier has been transmitted to a client system and/or to which client system, for example in order to detect intrusion.

After the client system 206 has received the message 232, the client system 206 may transmit a request message 236 to the source system. The request message may request the source system to provide the confidential information on the basis of the resource identifier. The request message 236 may comprise the resource identifier.

Optionally, after the source system has received message 236, the source system 202 and the client system 206 may establish a secure connection 238. After the secure connection 238 has been established, any further messages between the source system 202 and the client system 206 may be exchanged over connection 238. Connection 238 may be an encrypted https connection.

Optionally (not shown), the secure connection 238 is established prior to the client system transmitting message 236. In an example, prior to message 236 being sent, a handshake procedure occurs between the client system and the source system, e.g. according to the HTTPS protocol. After this handshake procedure, a TLS channel may be established through which message 236 is transmitted.

In embodiments the method comprises the source system 202 transmitting a message 240 to the client system, the message 240 comprising an instruction to provide the authorization code or to prove possession of the authorization code using, e.g., a challenge-response protocol, e.g., such as used for PIN validation in many systems to date. In response to receiving message 240, the client system 206 provides the authorization code in message 242. If the authorization code is to be provided directly, it is preferably provided via the secured connection established in step 238. Optionally (not shown) the authorization code may be provided to the source system in message 236, which obviates the challenge-response messages 240 and 242 for providing the authorization code to the source system 202.

In one embodiment, the source system 202, upon receiving message 236, and validating possession of the authorization code, may bind the resource identifier generated in step 210 to the client system 206, in particular to a key or PIN or (secret) code associated with the client system, for example possessed and only known to the client system 206, as a result of which binding only client system 206 may be able to use the resource identifier generated in step 210 to request access to the confidential information. In an example, the source system 202 may require that said key or PIN or (secret) code is provided by a client system requesting, using the resource identifier, access to the confidential information.

In embodiments the method comprises a step 243 retrieving the confidential information based on the received resource identifier received from the client system.

Message 244 may be transmitted from the client system to the source system 206 and may comprise the confidential information or a pointer and/or an authentication token with which the client system may be able to obtain the confidential information. It should be appreciated that message 244 may be transmitted on the basis of the received resource identifier and/or on the basis of the received authorization code. By transmitting message 244, the source system 206 may provide the client system 206 access to the confidential information. Message 244 may enable the client system to perform operations on and/or with the resource identifier, such as accessing/reading the confidential data, writing some information, making a copy of the resource identifier, for example as described in US 2014/0047513 A1. Message 244 may effectively bind the resource identifier to the client system 206.

In one embodiment, the source system may provide access based on information about the client system, such as information indicative of a role or specialty of a user or owner of the client system, for example information indicative of the medical profession of the user or owner of the client system.

In one embodiment, the source system may provide access based on a policy defining that said role or specialty is allowed to request the confidential information.

Optionally the client system 206 transmits a message 246 to the source system 202, the message comprising new confidential information of the person. The message 246 may request the source system or the owner of the source system or the maintainer of the confidential information at the source system to add this new confidential information to the confidential information stored at the source system, for example to add new information to a patient's record or to update the patient's record according to the content of the message.

Figure 2B:
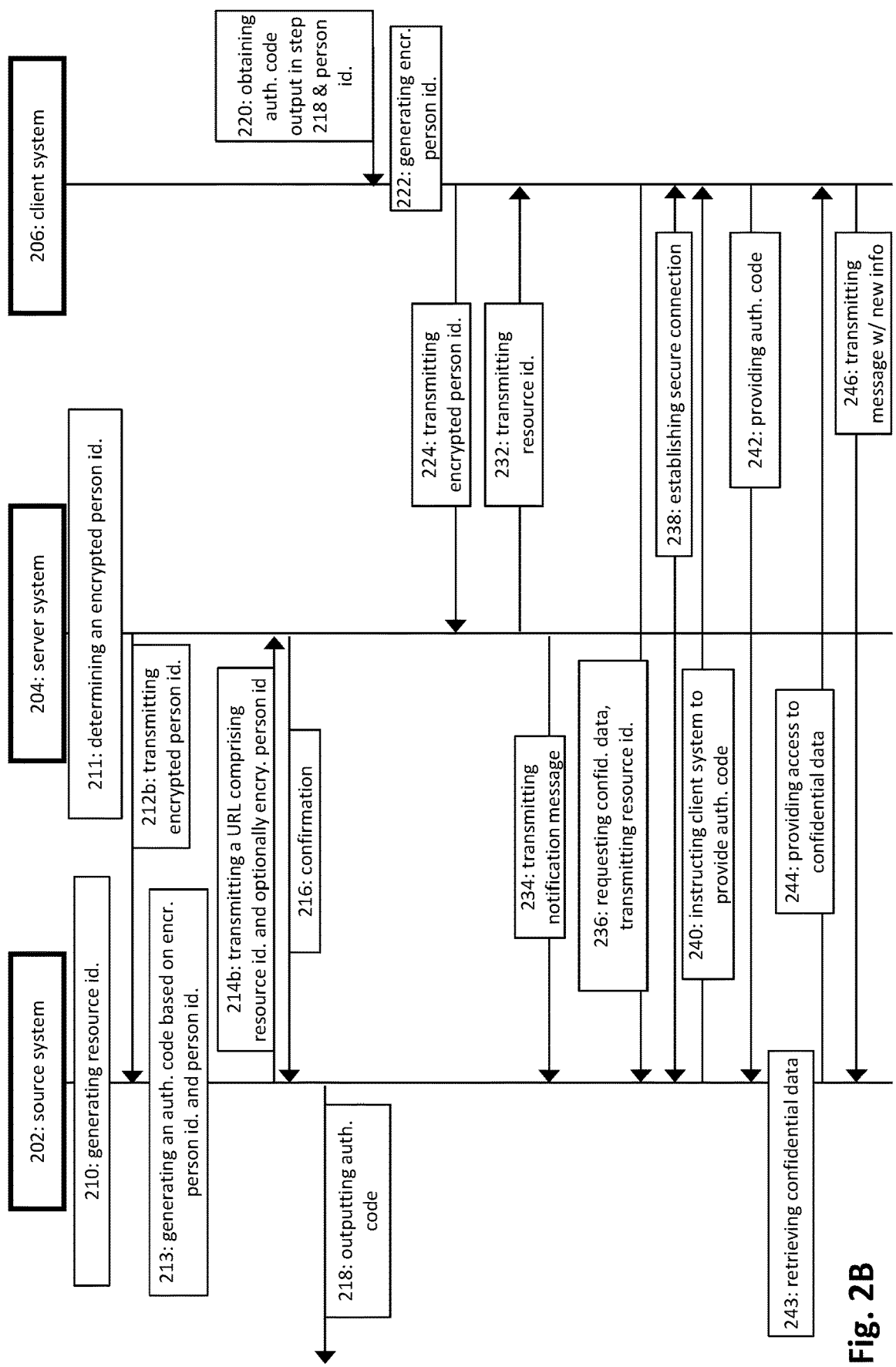

FIG. 2B is a flow chart illustrating other methods according to embodiments. Herein like reference numerals with respect to FIG. 2A denote similar steps and are not discussed for brevity. Steps 211, 212b, 213 and 214b are not shown in FIG. 2A. Step 211 comprises the server system 204 determining an encrypted person identifier. Preferably this encrypted identifier is not yet stored in association with a resource identifier in the server system. Step 212b comprises the server system transmitting the encrypted person identifier to the source system 202 and step 213 the source system using the encryption algorithm to generate the authorization code based on the encrypted person identifier and the person identifier. In step 214b, the source system 202 transmits a URL to the server system 204, wherein the URL comprises the generated resource identifier and wherein the URL optionally comprises the encrypted person identifier. With the transmittal of the URL the source system 202 may instruct the server system to store the encrypted person identifier in association with the URL or the resource identifier, including for example instructing the server system to store the URL comprising both the resource identifier and the encrypted person identifier.

FIGS. 3A and 3B respectively illustrate stored information in a storage 308 of a source system according to one embodiment of the invention and stored information in a registry 322 of a server system according to one embodiment of the invention. In these figures, the respective pieces of information in one row are associated with each other.

In FIG. 3A column "#" lists row numbers, column ID lists person identifiers, for example social security numbers of patients of a general practitioner that keeps medical records of his patients.

Column ID_contracted lists contracted person identifiers. The encryption algorithm may namely comprise contracting person identifiers to a particular number.

Column AC lists authorization codes, column EID lists encrypted person identifiers, which are the result of encrypting the person identifiers on the basis of the respective authorization codes in column AC. Column RI lists resource identifier.

As shown, the source system may be configured to store different resource identifiers for one and the same person. Note for example that the resource identifiers in rows 1, 2 and 3 are associated with the same person identified by person identifier "999901230", whereas the resource identifier in row 4 is associated with a person identified by "164154553" and the resource identifier in row 5 with yet another person identified by "265413".

It should be appreciated that for rows 1-4 holds that EID=(contracted ID) XOR AC and that AC=(contracted ID) XOR EID. In particular for row 1 that 795182=901230 XOR 123456 and that 123456=901230 XOR 795182. For row 5 holds that EID=ID XOR AC and AC=ID XOR EID.

It should be appreciated that the resource identifier depicted in FIGS. 3A and 3B has been simplified for purposes of clarity and that the resource identifier may comprise at least one of: ordering and separation characters, a <datatype> field, a <contenttype> field, a <contentsubtype> field, a <recordID> field, a <PIN=y|n|trust-binding> field, a <token> field, a <bind=y|n> field, a [bind-expiry] field, a <expiry> field, an <allow-renew=y|n> field, an <allow-copy=y|n> field, a <permissions> field, an [encryption-options] field, an [extensions] field as described in US 2014/0047513 A1, which is incorporated herein by reference in its entirety.

It should be appreciated that the fields are indicative of what may be in a resource identifier, e.g. a URL, and not restrictive, limitative or exhaustive, and that other or alternative field names may be used in concrete embodiments.

In these examples, the resource identifier is formatted as a URL and the resource identifier comprises an address of the source system 102, namely "sourcesyst102". The resource identifiers, in particular the pathnames "recordID=xxx", are indicative of a data storage location (e.g., a specific patient record) at the source system. Note that the resource identifiers in rows 1, 2 and 3 are different, yet these may all be indicative of the same data storage location—effectively, the record identifier thus can be a virtual identifier; this may be important to ensure that the resource identifier does not (indirectly) leak information that may help an attacker identify the patient, for example by matching the record identifier against other external records, e.g., de-identified records that contain the local (per-practice) patient identifiers, date of birth and postal code of patients. In an example, the source system has stored "recordID=9537" (row 1) in association with a particular data storage location, has stored "recordID=5674"(row 2) with that same particular data storage location and has stored "recordID=5735"(row 3) with that same particular data storage location.

In this example, the resource identifier in row 1 thus comprises "sourcesyst102" and "recordID=9537". This information may be transmitted to the server system together with the associated encrypted person identifier "795182". The server system may subsequently store the encrypted person identifier and the resource identifier in association with each other as shown in FIG. 3B. It should be appreciated that the source system may be configured to add the encrypted person identifier to the resource identifier and to transmit the resulting combination of encrypted person identifier and resource identifier to the server system, e.g. as described in FIG. 2B. With regards to the example shown in row 1 of FIG. 3A, the source system may thus transmit to the server system the URL:

"https://sourcesyst102.org/recordID=9537/ EID=795182", and the server system may store the resource identifier in association with the encrypted person identifier in the sense that it stores this aggregated URL.

In yet another example (not shown) the server system stores only a part of the resource identifier. To clarify using the information in row 1 of FIG. 3A, the server system may store "37" in association with encrypted person identifier "795182". The client system may obtain this part of the resource identifier "37" as explained above. In addition, the client system needs to obtain the rest of the URL, namely "https://sourcesyst102.org/recordID=95". The client system may obtain this missing part similar to how the client system can obtain the authorization code. In an example, this missing part is of the URL is comprised in the authorization code.

Additionally or alternatively, the authorization code may need to be incorporated in the URL to complete it before the client system can use the complete URL to connect to the source system. Only a client system which has obtained the secret authorization code can complete the URL, and only the complete URL—with the complete pathname including the authorization code constructed by the client using a convention—may be recognized by the source as a valid URL. This procedure avoids that the source system and the client system have to engage in a separate protocol to validate that the client system has access to the authorization code, after the URL's pathname is presented to the source system. An example of a completed URL (not shown), corresponding to row 1 of FIG. 3A, is: https://sourcesyst102.org/recordID=9537/tokenAC=1234561236/. Note that this completed URL is only known by the source system and the client system, and not stored at the server.

Since storage 308 has stored the authorization code in association with the resource identifier, the source system is able to perform an additional authorization step upon receiving a request message from a client system, the request message comprising the resource identifier. After all, the source system may also receive, optionally after transmitting an instruction to the client system to provide the authorization code, the authorization code from the client system or proof of possession thereof. Then, the source system may be configured to verify that it had already stored the authorization code in association with the resource identifier received from the client system. In response, the source system may provide access to the confidential information or a reference to that data by transmitting at least part of the confidential information to the client system.

FIG. 3B shows information that is stored in a registry 322 of a server system according to an embodiment. Apparently, the server system has received all of the resource identifier and associated encrypted person identifiers shown in FIG. 3A. In addition, the server system has also received and stored resource identifier from another source system 999 located at address "sourcesyst999". The server system may thus be configured to receive resource identifier and associated encrypted person identifiers from a plurality of source systems.

Figure 4:
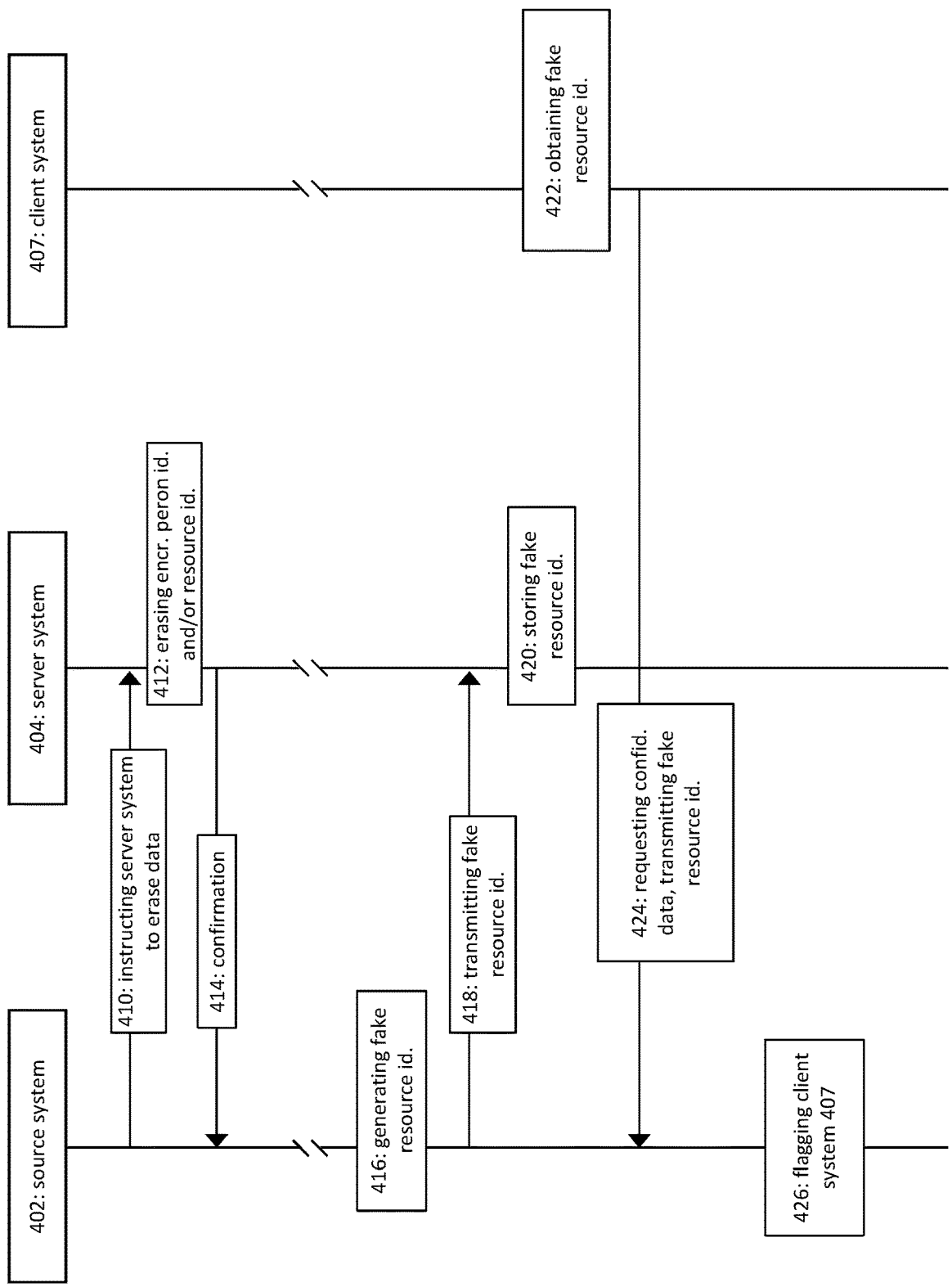
FIG. 4 is a flow chart illustrating further method steps according to embodiments of the invention.

FIG. 4 is a flow chart illustrating methods according to embodiments of the invention. These methods may be performed by a source system according to one embodiment of the invention, in particular by a source system 402 according to embodiments of the invention, by a server system 404 according to embodiments of the invention and by a second client system 407 according to embodiments of the invention.

One embodiment may comprise the source system 402 transmitting an instruction to the server system 404 to erase an encrypted person identifier and/or an associated resource identifier from [a registry of] the server system. In response to receiving instruction 410, the server system 404 may in step 412 erase the encrypted person identifier and/or the associated resource identifier from a registry of the server system 404. In these embodiments, the server system may transmit a confirmation 414 to the source system 402 that the encrypted person identifier and/or the associated resource identifier is/are erased from the registry of the server system 404.

In a separate embodiment, the method comprises the source system generating fake resource identifier and a fake encrypted person identifier, as indicated by step 416. The fake resource identifier may comprise a fake pointer to the data. However, the fake resource identifier may comprise an actual address of the source system 402. Then, the source system 401 may transmit a message 418 to the server system 404, the message 418 comprising the fake resource identifier and the fake identifier. The message 418 may instruct the server system 404 to store the fake resource identifier in association with the fake encrypted person identifier. In one example, message 418 comprises a URL that comprises both the fake resource identifier and the fake encrypted person identifier.

In response to receiving message 418 from the source system 402, the server system 404 may store the fake resource identifier and the fake person identifier in association with each other.

Step 422 depicts the second client system 407 obtaining the fake identifier and the fake resource identifier generated in step 416 by the source system 402. The second client system may have obtained these unlawfully. The second client system 407 may be associated with a malicious party, such as a hacker. In an example a hacker may have broken into the server system 404 and may have stolen information from the server system, among which information was the fake identifier and the fake resource identifier.

As said, the fake resource identifier may comprise an actual address of the source system 402. Hence, the second client system 407 may transmit the fake resource identifier and the fake identifier to the source system 402 in message 424 in an attempt to obtain confidential information from the source system 402. The message 424 may comprise a request to access data. It should be noted that this is of value when assuming that an attacker can, by using external information, derive the personal ID of a subject, e.g., based on the time of registration in combination with a news report, and by exhaustive search or some other method, generating the authorization code that, combined with the personal ID, resulted in the EID stored in the server system; with the use of fake IDs, the change is increased that an attacker is detected as the attacker has no way to distinguish fake from real EIDs and resource identifier stored in the server.

Upon reception of message 424, the source system 402 may flag the second client system 407 on the basis of the received fake resource identifier and/or on the basis of the fake identifier as indicated by step 426. In an example the source system 402 has stored the fake resource identifier and/or the fake person identifier the source system 402 itself generated in step 416. Upon the source system 402 determining that an incoming request for access to data comprises at least one of the fake resource identifier, such as a fake pointer to data, ?? the fake encrypted person identifier, the source system may flag the second client system and/or a user of the second client system, e.g. flag as potentially malicious.

As a result of the flagging, the source system 402 may deny any request for data that is received from (the user of) second client system 407.

Figure 5:
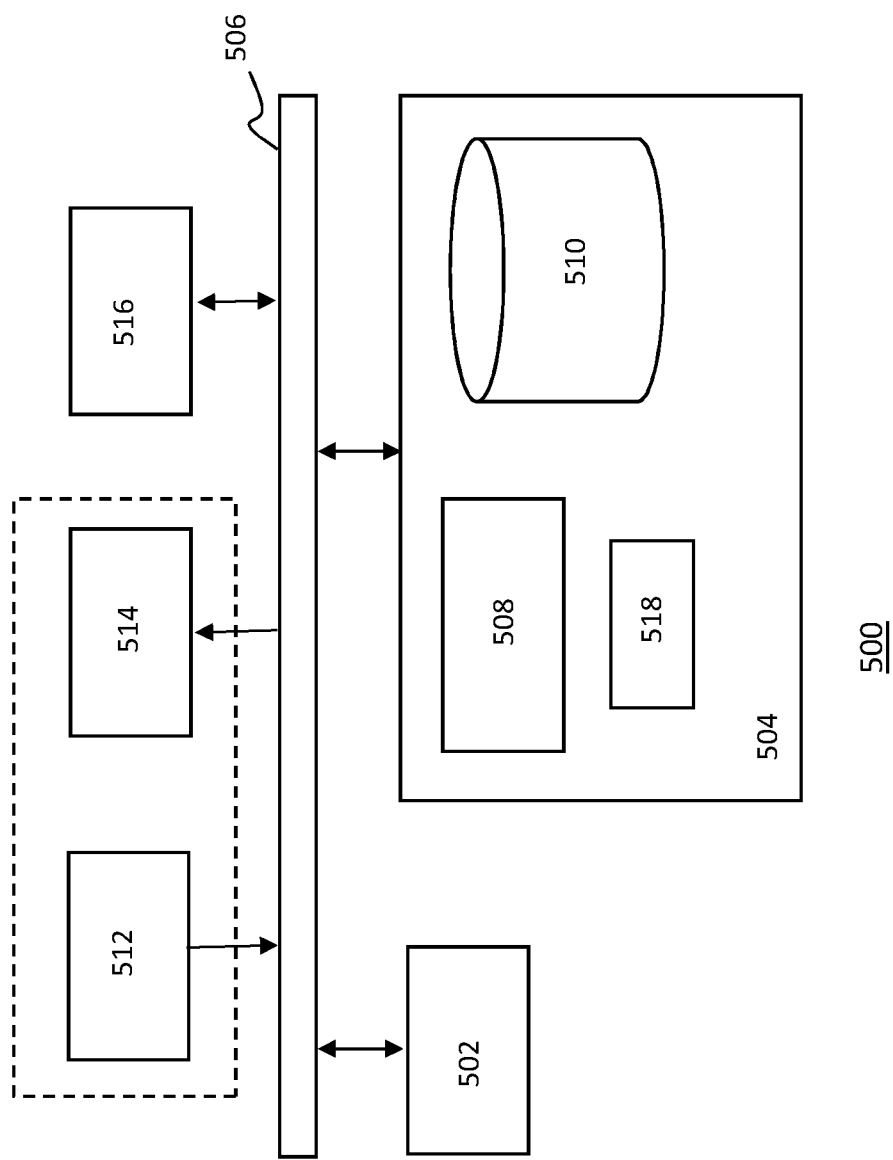
FIG. 5 depicts a computing system, according to one embodiment of the present invention.

FIG. 5 depicts a block diagram illustrating an exemplary data processing system according to one embodiment of the invention.

As shown in FIG. 5, the data processing system 500 may include at least one processor 502 coupled to memory elements 504 through a system bus 506. As such, the data processing system may store program code within memory elements 504. Further, the processor 502 may execute the program code accessed from the memory elements 504 via a system bus 506. In one aspect, the data processing system may be implemented as a computer that is suitable for storing and/or executing program code. It should be appreciated, however, that the data processing system 500 may be implemented in the form of any system including a processor and a memory that is capable of performing the functions described within this specification.

The memory elements 504 may include one or more physical memory devices such as, for example, local memory 508 and one or more bulk storage devices 510. The local memory may refer to random access memory or other non-persistent memory device(s) generally used during actual execution of the program code. A bulk storage device may be implemented as a hard drive or other persistent data storage device. The processing system 500 may also include one or more cache memories (not shown) that provide temporary storage of at least some program code in order to reduce the number of times program code must be retrieved from the bulk storage device 510 during execution.

Input/output (I/O) devices depicted as an input device 512 and an output device 514 optionally can be coupled to the data processing system. Examples of input devices may include, but are not limited to, a keyboard, a pointing device such as a mouse, or the like. Examples of output devices may include, but are not limited to, a monitor or a display, speakers, or the like. Input and/or output devices may be coupled to the data processing system either directly or through intervening I/O controllers.

In an embodiment, the input and the output devices may be implemented as a combined input/output device (illustrated in FIG. 5 with a dashed line surrounding the input device 512 and the output device 514). An example of such a combined device is a touch sensitive display, also sometimes referred to as a "touch screen display" or simply "touch screen". In such an embodiment, input to the device may be provided by a movement of a physical object, such as e.g. a stylus or a finger of a user, on or near the touch screen display.

A network adapter 516 may also be coupled to the data processing system to enable it to become coupled to other systems, computer systems, remote network devices, and/or remote storage devices through intervening private or public networks. The network adapter may comprise a data receiver for receiving data that is transmitted by said systems, devices and/or networks to the data processing system 500, and a data transmitter for transmitting data from the data processing system 500 to said systems, devices and/or networks. Modems, cable modems, and Ethernet cards are examples of different types of network adapter that may be used with the data processing system 500.

As pictured in FIG. 5, the memory elements 504 may store an application 518. In various embodiments, the application x18 may be stored in the local memory 508, the one or more bulk storage devices 510, or apart from the local memory and the bulk storage devices. It should be appreciated that the data processing system 500 may further execute an operating system (not shown in FIG. 5) that can facilitate execution of the application 518. The application 518, being implemented in the form of executable program code, can be executed by the data processing system 500, e.g., by the processor 502. Responsive to executing the application, the data processing system 500 may be configured to perform one or more operations or method steps described herein.

In one aspect of the present invention, the data processing system 500 may represent a server system and/or a source system and/or a client system as described herein.

In another aspect, the data processing system 500 may represent a client data processing system. In that case, the application 518 may represent a client application that, when executed, configures the data processing system 500 to perform the various functions described herein with reference to a "client". Examples of a client can include, but are not limited to, a personal computer, a portable computer, a mobile phone, or the like.

In yet another aspect, the data processing system 500 may represent a server. For example, the data processing system may represent an (HTTP(s)) server, in which case the application 518, when executed, may configure the data processing system to perform (HTTP(s)) server operations.

Various embodiments of the invention may be implemented as a program product for use with a computer system, where the program(s) of the program product define functions of the embodiments (including the methods described herein). In one embodiment, the program(s) can be contained on a variety of non-transitory computer-readable storage media, where, as used herein, the expression "non-transitory computer readable storage media" comprises all computer-readable media, with the sole exception being a transitory, propagating signal. In another embodiment, the program(s) can be contained on a variety of transitory computer-readable storage media. Illustrative computer-readable storage media include, but are not limited to: (i) non-writable storage media (e.g., read-only memory devices within a computer such as CD-ROM disks readable by a CD-ROM drive, ROM chips or any type of solid-state non-volatile semiconductor memory) on which information is permanently stored; and (ii) writable storage media (e.g., flash memory, floppy disks within a diskette drive or hard-disk drive or any type of solid-state random-access semiconductor memory) on which alterable information is stored. The computer program may be run on the processor 502 described herein.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of embodiments of the present invention has been presented for purposes of illustration, but is not intended to be exhaustive or limited to the implementations in the form disclosed. Many modifications and variations will be apparent to those of ordinary skill in the art without departing from the scope and spirit of the present invention. The embodiments were chosen and described in order to best explain the principles and some practical applications of the present invention, and to enable others of ordinary skill in the art to understand the present invention for various embodiments with various modifications as are suited to the particular use contemplated.

The invention claimed is:

1. A method for providing a client access to confidential information of a person stored at a source system, the client accesses the confidential information using a resource identifier, the client and the source system comprising an encryption module for executing an encryption algorithm, the method comprising: the source system generating the resource identifier, the resource identifier comprising a URL, the resource identifier being indicative of a data storage location at the source system, the data storage location comprising the confidential information of the person, the person being identified by a person identifier; the source system obtaining, by generating or receiving, a first code; the source system using the encryption algorithm for generating a second code based on the first code and based on the person identifier; the source system transmitting a message to a server system, the message comprising at least part of the resource identifier, the message instructing the server system to store the first code or the second code as an encrypted person identifier in association with the at least part of the
  as authorization code to a trusted communication path for delivery of the authorization code to the client; the source system receiving from a client a request to access the confidential information associated with the person identifier, wherein the client receives the authorization code via the trusted communication path and to receive the person identifier in order to generate the encrypted person identifier based on the received authorization code and based on the received person identifier using the encryption algorithm; and to retrieve the at least part of the resource identifier from the server system on the basis of the generated encrypted person identifier; and, to use the at least part of the resource identifier for sending the request to the source system; the source system providing the client access to the confidential information on the basis of the request received from the client, wherein providing access includes retrieving the confidential information from the data storage location and transmitting at least part of the confidential information to the client.

2. The method according to claim 1, wherein
  the message from the source system to the server system instructs the server system to store the second code as the encrypted person identifier in association with the at least part of the resource identifier, and wherein
  the source system provides the first code as the authorization code to the trusted communication path.

3. The method according to claim 1, wherein the encryption algorithm is a reversible encryption algorithm and wherein
  the message from the source system to the server system instructs the server system to store the first code as the encrypted person identifier in association with the at least part of the resource identifier, and wherein
  the source system provides the second code as the authorization code to the trusted communication path.

4. The method according to claim 1, further comprising the source system receiving the first code from the server system.

5. The method according to claim 1, wherein the message from the source system to the server system comprises a first part of the resource identifier, the method further comprising the source system providing a second part of the resource identifier to the trusted communication path and/or to a second trusted communication path for delivery to the client, wherein the client is adapted to receive the second part of the resource identifier via the trusted communication path and/or via the second trusted communication path respectively and to use the first part of the resource identifier and the second part of the resource identifier to construct the resource identifier for sending the request to the source system.

6. The method according to claim 1, further comprising: the source system receiving from the client the authorization code received by the client; and the source system providing the client access to the confidential information on the basis of the received request message and on the basis of the authorization code received from the client.

7. The method according to claim 1, further comprising: in response to receiving the request message from the client, instructing the client to provide the authorization code.

8. The method according to claim 1, further comprising:
  the source system instructing the server system to erase the encrypted person identifier and the associated resource identifier from the server system.

9. The method according to claim 1, further comprising: the source system generating a fake resource identifier and optionally a fake person identifier; and the source system transmitting a second message to the server system, the second message comprising the fake resource identifier and optionally the fake person identifier, the second message instructing the server system to store the fake resource identifier optionally in association with the fake identifier; the source system receiving from a second client a second request to access data, determining that the fake resource identifier was used by the second client for sending the second request to the source system, e.g. by determining that the second request comprises the fake resource identifier; and in response flagging the second client.

10. A source system for providing a client access to confidential information of a person stored at a source system, the client accesses the confidential information using a resource identifier, the client and the source system comprising an encryption module for executing an encryption algorithm, the source system comprising: a non-transitory computer readable storage medium having least part of a program embodied therewith; and, a non-transitory computer readable storage medium having computer readable program code embodied therewith, and a processor coupled to the non-transitory computer readable storage medium, wherein responsive to executing the computer readable program code, the processor is configured to perform executable operations comprising: generating the resource identifier, the resource identifier comprising a URL, the resource identifier being indicative of a data storage location at the source system, the data storage location comprising the confidential information of the person, the person being identified by a person identifier; obtaining, generating or receiving, a first code; using the encryption algorithm for generating a second code based on the first code and based on the person identifier; transmitting a message to a server system, the message comprising at least part of the resource identifier, the message instructing the server system to store the first code or the second code as an encrypted person identifier in association with the at least part of the resource identifier; providing the second code or the first code respectively as authorization code to a trusted communication path for delivery of the authorization code to the client; receiving from a client a request to access the confidential information associated with the person identifier, wherein the client is adapted to receive the authorization code via the trusted communication path and to receive the person identifier in order to generate the encrypted person identifier based on the received authorization code and based on the received person identifier using the encryption algorithm; and to retrieve the at least part of the resource identifier from the server system on the basis of the generated encrypted person identifier; and, to use the at least part of the resource identifier for sending the request to the source system; providing the client access to the confidential information on the basis of the request received from the client, wherein providing access includes retrieving the confidential information from the data storage location and transmitting at least part of the confidential information to the client.

11. A method for a client for accessing confidential information of a person stored at a source system, the client the confidential information using a resource identifier, the client and the source system comprising an encryption module for executing an encryption algorithm, wherein the source system is configured to generate the resource identifier, preferably the resource identifier comprising a URL, the resource identifier being indicative of a data storage location at the source system, the data storage location comprising the confidential information of the person, the person being identified by a person identifier, and to obtain, generating or receiving, a first code; and to use the encryption algorithm for generating a second code based on the first code and based on the person identifier; and to transmit a message to a server system, the message comprising at least part of the resource identifier, the message instructing the server system to store the first code or the second code as an encrypted person identifier in association with the at least part of the resource identifier; and to provide the second code or the first code respectively as authorization code to a trusted communication path for delivery of the authorization code to the client; the method comprising: the client receiving the authorization code via the trusted communication path; the client receiving the person identifier; the client using the encryption algorithm to generate the encrypted person identifier based on the received authorization code and based on the received person identifier; the client transmitting a request message to the server system, the request message comprising the encrypted person identifier as generated by the client, the request message requesting the server system to provide the at least part of the resource identifier; the client receiving the at least part of the resource identifier from the server system; the client using the at least part of the resource identifier for sending a request to access the confidential information to the source system; wherein the source system is configured to provide the client access to the confidential information on the basis of the request received from the client, the method further comprising the client gaining access to the confidential information by receiving at least part of the confidential information from the source system.

* * * * *

UNITED STATES PATENT AND TRADEMARK OFFICE
CERTIFICATE OF CORRECTION

| | |
|---|---|
| PATENT NO. | : 11,328,090 B2 |
| APPLICATION NO. | : 16/633913 |
| DATED | : May 10, 2022 |
| INVENTOR(S) | : Guido Johannes van't Noordende |

It is certified that error appears in the above-identified patent and that said Letters Patent is hereby corrected as shown below:

In the Claims

Column 33, Lines 62-63, Claim 1, delete "the as" and insert -- the resource identifier; the source system providing the second code or the first code respectively as --

Column 35, Line 5, Claim 9, delete "system, e.g. by" and insert -- system by --

Column 35, Line 14, Claim 10, delete "having" and insert -- having at --

Column 36, Lines 7-8, Claim 11, delete "client the" and insert -- client accesses the --

Signed and Sealed this
Thirtieth Day of August, 2022

*Katherine Kelly Vidal*

Katherine Kelly Vidal
*Director of the United States Patent and Trademark Office*